United States Patent
Slingluff et al.

(10) Patent No.: US 6,558,671 B1
(45) Date of Patent: May 6, 2003

(54) CYSTEINE-DEPLETED PEPTIDES RECOGNIZED BY A3-RESTRICTED CYTOTOXIC LYMPHOCYTES, AND USES THEREFOR

(75) Inventors: Craig L. Slingluff; Donald F. Hunt; Victor H. Engelhard; David Kittlesen, all of Charlottesville, VA (US)

(73) Assignee: The University of Virginia Patent Foundation, Charlottesville, VA (US)

(*) Notice: Subject to any disclaimer, the term of this patent is extended or adjusted under 35 U.S.C. 154(b) by 0 days.

(21) Appl. No.: 09/341,982
(22) PCT Filed: Jan. 29, 1998
(86) PCT No.: PCT/US98/01592
§ 371 (c)(1), (2), (4) Date: Sep. 20, 1999
(87) PCT Pub. No.: WO98/33810
PCT Pub. Date: Aug. 6, 1998

Related U.S. Application Data

(60) Provisional application No. 60/037,781, filed on Jan. 31, 1997.

(51) Int. Cl.[7] ............................................. A61K 39/00
(52) U.S. Cl. ........................ 424/185.1; 424/184.1; 424/193.1; 435/7.1; 435/7.24; 435/173.4; 435/173.7; 530/300; 530/326; 530/327; 530/328; 530/403
(58) Field of Search .................... 424/185.1, 193.1, 424/184.1; 435/7.1, 7.24, 173.4, 173.7; 530/300, 326, 328, 403, 327

(56) References Cited

U.S. PATENT DOCUMENTS

| | | |
|---|---|---|
| 4,518,584 A | 5/1985 | Mark et al. |
| 4,572,798 A | 2/1986 | Koths et al. |
| 4,588,585 A | 5/1986 | Mark et al. |
| 4,737,462 A | 4/1988 | Mark et al. |
| 4,959,314 A | 9/1990 | Mark et al. |
| 5,359,034 A | 10/1994 | Skelly et al. |
| 5,409,897 A | 4/1995 | Thomas et al. |
| 5,773,253 A | 6/1998 | Linsley et al. |
| 5,831,008 A | 11/1998 | Huang |
| 5,844,088 A | 12/1998 | Hoffman et al. |
| 5,874,238 A | 2/1999 | Potempa et al. |
| 5,908,762 A | 6/1999 | Ono et al. |
| 6,008,026 A | 12/1999 | Day |
| 6,087,122 A | 7/2000 | Hustad et al. |
| 6,124,114 A | 9/2000 | Hoffman et al. |

FOREIGN PATENT DOCUMENTS

| | | |
|---|---|---|
| WO | WO 94/14459 | 7/1994 |
| WO | WO 97/40156 | 10/1997 |

OTHER PUBLICATIONS

Ngo et al., 1994, The Protein Folding Problem and Tertiary Structure Prediction, pp. 492–495.*
Fasano A Innovative strategies for the oral delivery of drugs and peptides. Trends in Biotechnology. vol. 16, No. 4 (1998) pp. 152–157.*
Pettit et al. The development of site–specific drug–delivery systems for protein and peptide biopharmaceuticals. Trends in Biotechnology. vol. 16, No. 8 (1998) pp. 343–349.*
Brandon et al. Introduction to protein stucture. Garland Publishing Inc., New York (1991) pp. 11–15.*
Engelhard V.H., "Structure of peptides associated with class I and classII MHC molecules." Annual Review of Immunology vol. 12 (1994), pp. 181–207.*
Wolfel et al.; Two tyrosinase nonapeptides recognized on HLA–A2 melanomas by autologous cytolytic T lymphocytes. European Journal of Immunology. vol. 24 (1994), pp. 759–764.*
Hioe et al.; Comparison of adjuvant formulations for cytotoxic T cell induction using synthetic peptides. Vaccine. vol. 14 (1996), pp. 412–418.*
Rock et al.; Peptide–priming of cytolytic T cell immunity in vivo using beta 2–microglobulin as an adjuvant Journal of Immunology. vol. 150 (1993), pp. 1244–1252.*
Carbone et al. Class I– resticted processing and presentation of exogenous cell associated antigen in vivo. Journal of Experimental Medicine. vol. 171 (1990), pp. 377–387.*
Kesari, K.V. et al., "A single amino acid substitution in the H–2kb molecule generates a defined allogenic epitope.", Mol. Immunol., vol. 30, No. 18, 1993, pp. 1671–1677.
Pointdexter, Nancy et al., "Isolation of a kidney–specific peptide recognized by alloreative HLA–A3– restricted human CTL.", J.Immunol., vol. 154, No. 8, 1995, pp. 3880–3887.

* cited by examiner

Primary Examiner—James Housel
Assistant Examiner—Ulrike Winkler
(74) Attorney, Agent, or Firm—Iver P. Cooper

(57) ABSTRACT

Cysteine-depleted CTL epitopes can elicit a stronger or more specific CTL response than the native, cysteine-containing CTL epitope of a disease associated antigen.

12 Claims, 10 Drawing Sheets

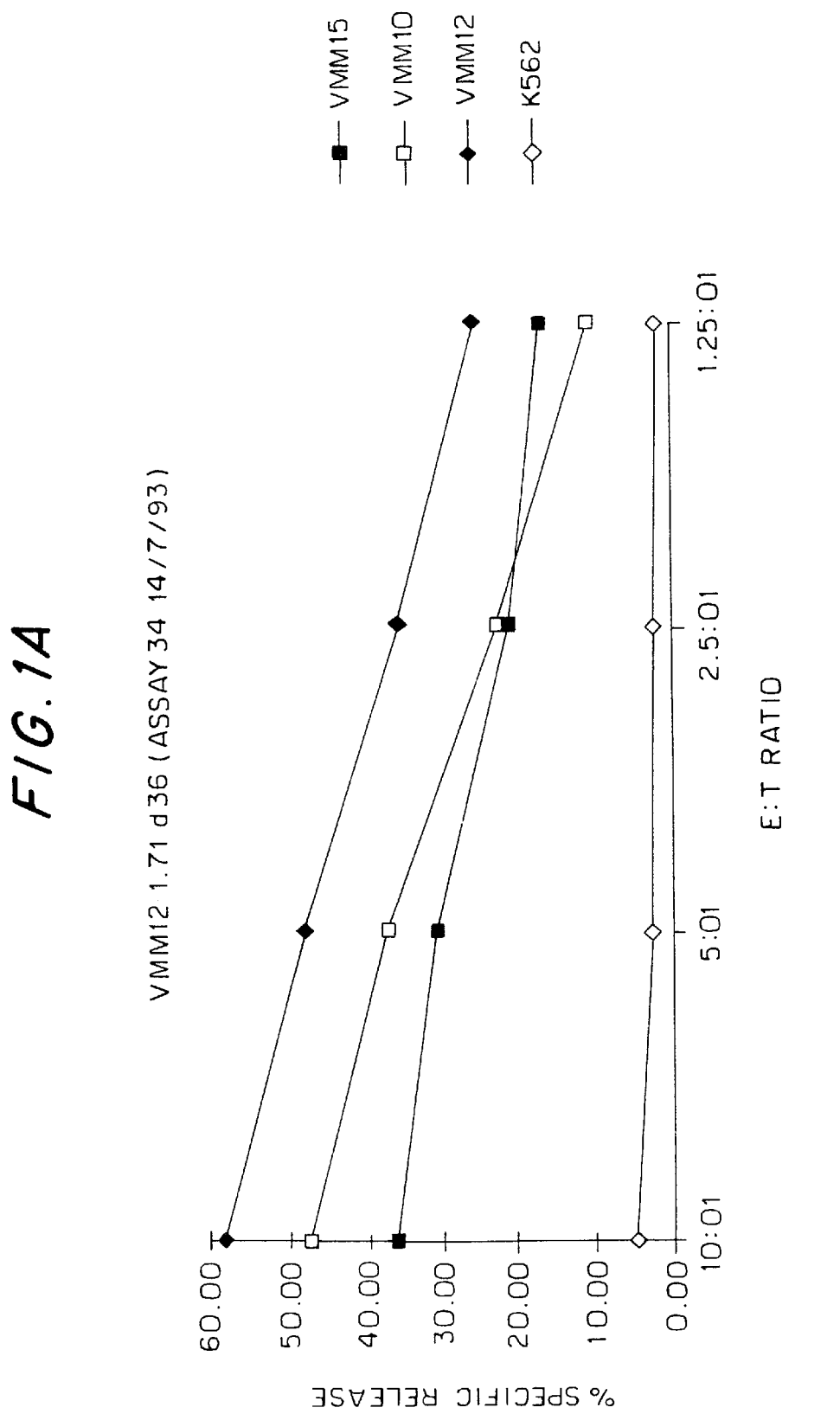

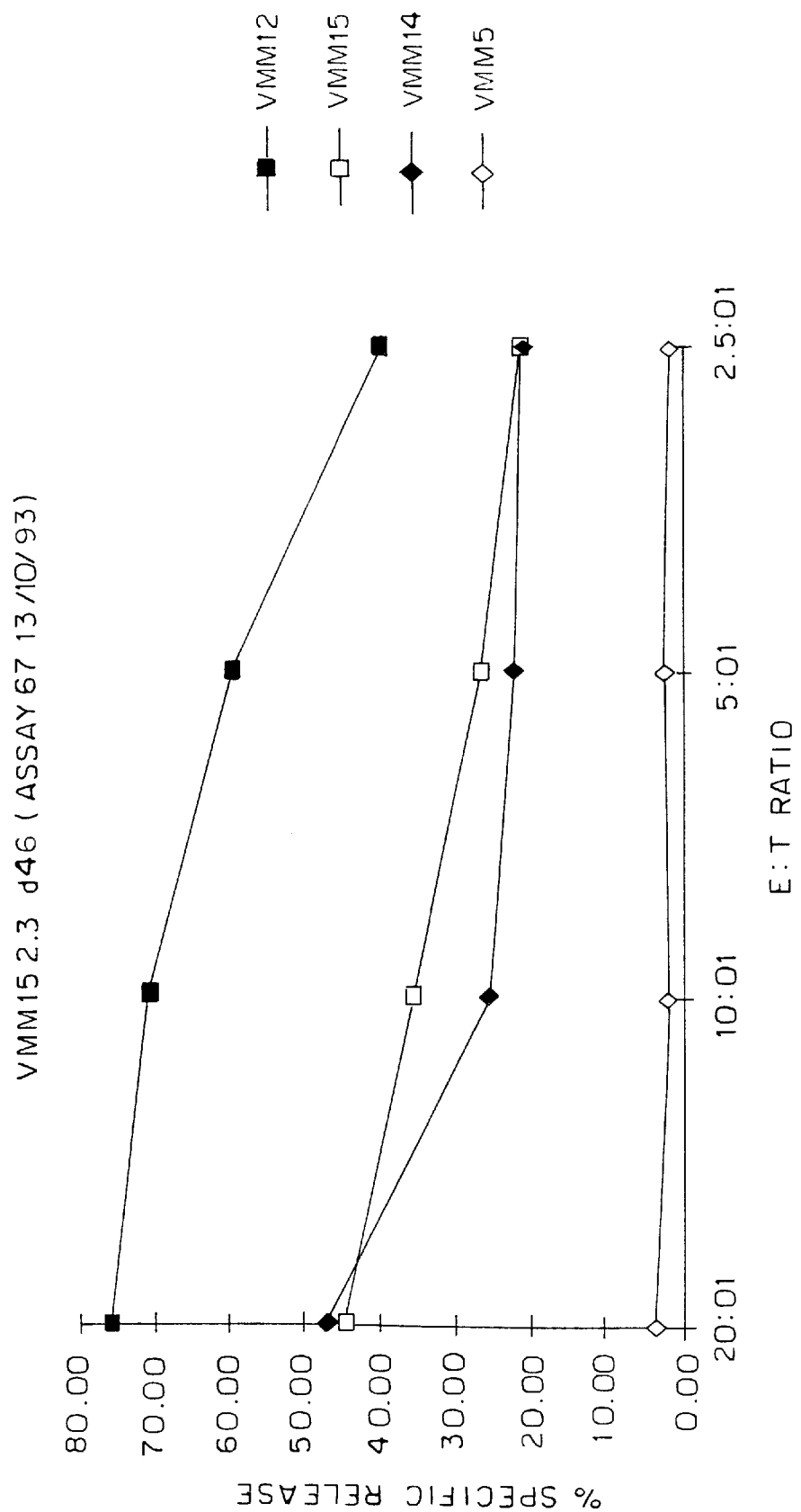

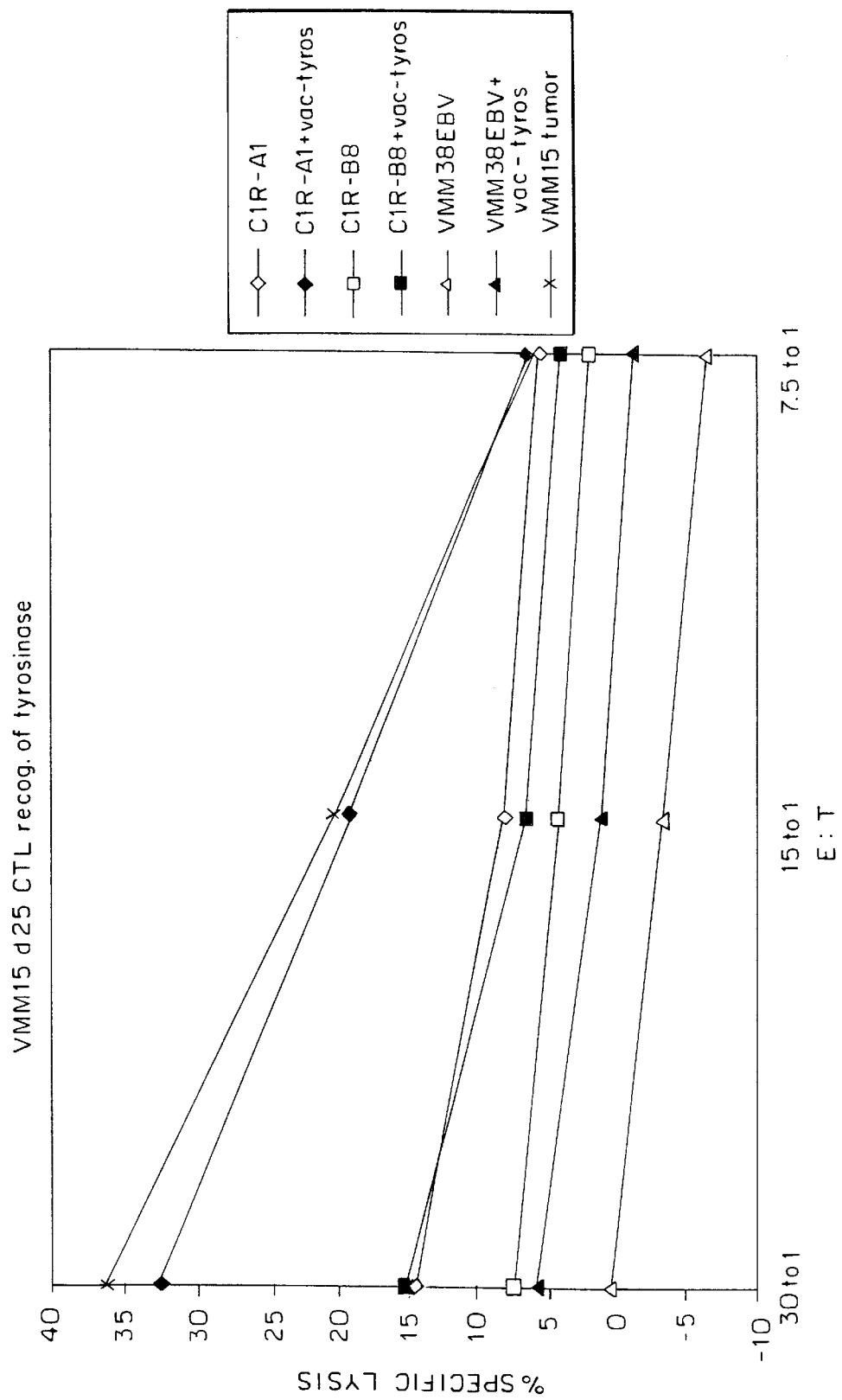

FIG. 5

Figure 2A:
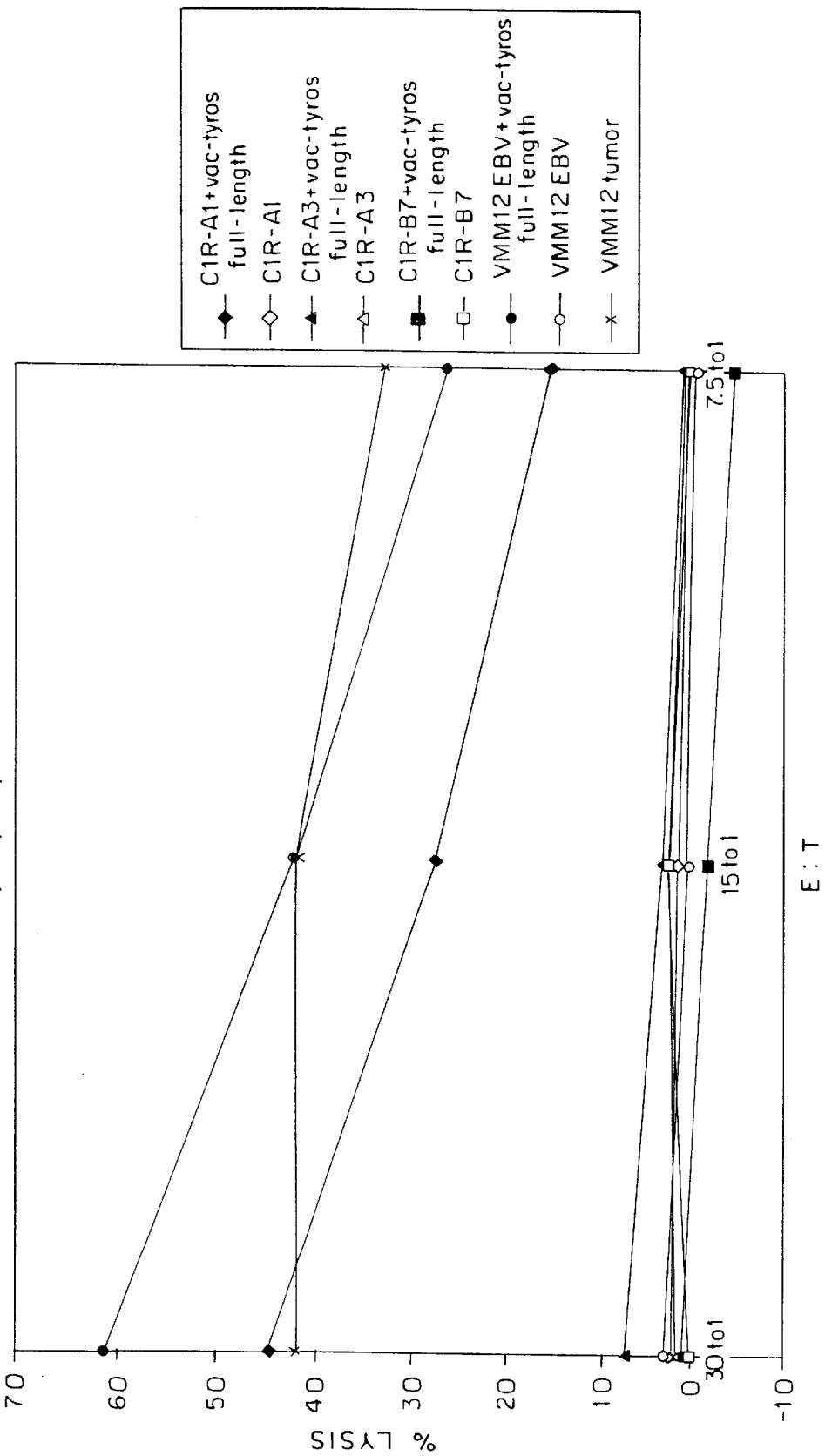

```
  1  MLLAVLYCLL WSFQTSAGHF PRACVSSKNL MEKECCPPWS GDRSPCGQLS
 51  GRGSCQNILL SNAPLGPQFP FTGVDDRESW PSVFYNRTCQ CSGNFMGFNC
101  GNCKFGFWGP NCTERRLLVR RNIFDLSAPE KDKFFAYLTL AKHTISSDYV
151  IPIGTYGQMK NGSTPMFNDI NIYDLFVWMH YYVSMDALLG GSEIWRDIDF
201  AHEAPAFLPW HRLFLLRWEQ EIQKLTGDEN FTIPYWDWRD AEKCDICTDE
251  YMGGQHPTNP NLLSPASFFS SWQIVCSRLE EYNSHQSLCN GTPEGPLRRN
301  PGNHDKSRTP RLPSSADVEF CLSLTQYESG SMDKAANFSF RNTLEGFASP
351  LTGIADASQS SMHNALHIYM NGTMSQVQGS ANDPIFLLHH AFVDSIFEQW
401  LQRHRPLQEV YPEANAPIGH NRESYMVPFI PLYRNGDFFI SSKDLGYDYS
451  YLQDSDPDSF QDYIKSYLEQ ASRIWSWLLG AAMVGAVLTA LLAGLVSLLC
501  RHKRKQLPEE KQPLLMEKED YHSLYQSHL
```

KCDICTDEY represents residues 243-251 of the tyrosinase sequence

17/529 Residues are Cysteine       = 3.2%    2/9 Residues of KCDICTDEY are Cysteine      = 22%
30/529 Residues are Aspartic acid  = 5.7%    2/9 Residues of KCDICTDEY are Asp Acid      = 22%
27/529 Residues are Glutamic acid  = 5.1%    3/9 Residues of KCDICTDEY are Glutamic acid = 11%
17/529 Residues are Lysine         = 3.2%    1/9 Residues of KCDICTDEY are Cysteine      = 11%
Total of C-D-E-K               = 17.2%                                                 67%

SEQUENCE LISTING

```
<160> NUMBER OF SEQ ID NOS: 104

<210> SEQ ID NO 1
<211> LENGTH: 529
<212> TYPE: PRT
<213> ORGANISM: Homo sapiens

<400> SEQUENCE: 1

Met Leu Leu Ala Val Leu Tyr Cys Leu Leu Trp Ser Phe Gln Thr Ser
 1               5                  10                  15

Ala Gly His Phe Pro Arg Ala Cys Val Ser Ser Lys Asn Leu Met Glu
                20                  25                  30

Lys Glu Cys Cys Pro Pro Trp Ser Gly Asp Arg Ser Pro Cys Gly Gln
            35                  40                  45

Leu Ser Gly Arg Gly Ser Cys Gln Asn Ile Leu Leu Ser Asn Ala Pro
        50                  55                  60

Leu Gly Pro Gln Phe Pro Phe Thr Gly Val Asp Asp Arg Glu Ser Trp
 65                  70                  75                  80

Pro Ser Val Phe Tyr Asn Arg Thr Cys Gln Cys Ser Gly Asn Phe Met
                 85                  90                  95

Gly Phe Asn Cys Gly Asn Cys Lys Phe Gly Phe Trp Gly Pro Asn Cys
            100                 105                 110

Thr Glu Arg Arg Leu Leu Val Arg Arg Asn Ile Phe Asp Leu Ser Ala
        115                 120                 125

Pro Glu Lys Asp Lys Phe Phe Ala Tyr Leu Thr Leu Ala Lys His Thr
    130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Met Asp Ala Leu Leu Gly Gly Ser
            180                 185                 190

Glu Ile Trp Arg Asp Ile Asp Phe Ala His Glu Ala Pro Ala Phe Leu
        195                 200                 205

Pro Trp His Arg Leu Phe Leu Leu Arg Trp Glu Gln Glu Ile Gln Lys
    210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
                245                 250                 255
```

```
Pro Thr Asn Pro Asn Leu Leu Ser Pro Ala Ser Phe Phe Ser Ser Trp
        260                 265                 270

Gln Ile Val Cys Ser Arg Leu Glu Glu Tyr Asn Ser His Gln Ser Leu
            275                 280                 285

Cys Asn Gly Thr Pro Glu Gly Pro Leu Arg Arg Asn Pro Gly Asn His
        290                 295                 300

Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
                325                 330                 335

Asn Phe Ser Phe Arg Asn Thr Leu Glu Gly Phe Ala Ser Pro Leu Thr
                340                 345                 350

Gly Ile Ala Asp Ala Ser Gln Ser Ser Met His Asn Ala Leu His Ile
            355                 360                 365

Tyr Met Asn Gly Thr Met Ser Gln Val Gln Gly Ser Ala Asn Asp Pro
        370                 375                 380

Ile Phe Leu Leu His His Ala Phe Val Asp Ser Ile Phe Glu Gln Trp
385                 390                 395                 400

Leu Gln Arg His Arg Pro Leu Gln Glu Val Tyr Pro Glu Ala Asn Ala
                405                 410                 415

Pro Ile Gly His Asn Arg Glu Ser Tyr Met Val Pro Phe Ile Pro Leu
                420                 425                 430

Tyr Arg Asn Gly Asp Phe Phe Ile Ser Ser Lys Asp Leu Gly Tyr Asp
            435                 440                 445

Tyr Ser Tyr Leu Gln Asp Ser Asp Pro Asp Ser Phe Gln Asp Tyr Ile
        450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
                485                 490                 495

Ser Leu Leu Cys Arg His Lys Arg Lys Gln Leu Pro Glu Glu Lys Gln
            500                 505                 510

Pro Leu Leu Met Glu Lys Glu Asp Tyr His Ser Leu Tyr Gln Ser His
        515                 520                 525

Leu

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 2

Ala Asn Ala Pro Ile Gly His Asn Arg Glu Ser Tyr
  1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 3

Leu Gln Asp Ser Asp Pro Asp Ser Phe Gln Asp Tyr
```

-continued

```
<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 4

Asp Val Glu Phe Cys Leu Ser Leu Thr Gln Tyr
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 5

Gln Asp Ser Asp Pro Asp Ser Phe Gln Asp Tyr
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 6

Ser Thr Pro Met Phe Asn Asp Ile Asn Ile Tyr
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 7

Arg Arg His Arg Pro Leu Gln Glu Val Tyr
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 8

Ser Tyr Met Val Pro Phe Ile Pro Leu Tyr
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Fragment of
``` human protein

<400> SEQUENCE: 9

Val Ser Met Asp Ala Leu Leu Gly Gly Tyr
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 10

Asp Ala Glu Lys Cys Asp Ile Cys Thr Asp Glu Tyr
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 11

Leu Ser Ala Pro Glu Lys Asp Lys Phe Phe Ala Tyr
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 12

Glu Ser Tyr Met Val Pro Phe Ile Pro Leu Tyr
 1               5                  10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 13

Gln Ser Ser Met His Asn Ala Leu His Ile Tyr
 1               5                  10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 14

Thr Leu Ala Lys His Thr Ile Ser Ser Asp Tyr
 1               5                  10

<210> SEQ ID NO 15

```
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 15

Ser Asp Tyr Val Ile Pro Ile Gly Thr Tyr
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 16

Thr Gly Asp Glu Asp Phe Thr Ile Pro Tyr
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 17

Gln Arg His Arg Pro Leu Gln Glu Val Tyr
 1               5                  10

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 18

Pro Met Phe Asn Asp Ile Asn Ile Tyr
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 19

Lys Cys Asp Ile Cys Thr Asp Glu Tyr
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 20
```

Ser Met His Asn Ala Leu His Ile Tyr
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 21

Gly Asp Glu Asn Phe Thr Ile Pro Tyr
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 22

Ala Lys His Thr Ile Ser Ser Asp Tyr
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 23

Asp Tyr Val Ile Pro Ile Gly Thr Tyr
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 24

Ile Val Cys Ser Arg Leu Glu Glu Tyr
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 25

Glu Phe Cys Leu Ser Leu Thr Gln Tyr
1               5

<210> SEQ ID NO 26
<211> LENGTH: 9
<212> TYPE: PRT
<213> ORGANISM: Artificial Sequence
<220> FEATURE:

```
<223> OTHER INFORMATION: Description of Artificial Sequence: Fragment of
      human protein

<400> SEQUENCE: 26

Asp Leu Phe Val Trp Met His Tyr Tyr
  1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 27

Gly Asp Glu Asp Phe Thr Ile Pro Tyr
  1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 28

Gln Tyr Glu Ser Gly Ser Met Asp Lys
  1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 29

Phe Thr Ile Pro Tyr Trp Asp Trp Arg
  1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 30

Ser Ser Asp Tyr Val Ile Pro Ile Gly
  1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 31

Cys Thr Asp Glu Tyr Met Gly Gly Gln
  1               5
```

```
<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 32

Gly Thr Pro Glu Gly Pro Leu Arg Arg
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 33

Tyr Trp Asp Trp Arg Asp Ala Glu Lys
 1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 34

Ser Ser Met His Asn Ala Leu His Ile Tyr
 1               5                  10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 35

Ile Tyr Asp Leu Phe Val Trp Met His Tyr
 1               5                  10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 36

Thr Gly Asp Glu Asn Phe Thr Ile Pro Tyr
 1               5                  10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 37
```

Glu Lys Cys Asp Ile Cys Thr Asp Glu Tyr
 1               5                  10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 38

Thr Gly Asp Glu Asp Phe Thr Ile Pro Tyr
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 39

Thr Pro Met Phe Asn Asp Ile Asn Ile Tyr
 1               5                  10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 40

Val Glu Phe Cys Leu Ser Leu Thr Gln Tyr
 1               5                  10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 41

Gly Ser Glu Ile Trp Arg Asp Ile Asp Phe
 1               5                  10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 42

Gln Ile Val Cys Ser Arg Leu Glu Glu Tyr
 1               5                  10

<210> SEQ ID NO 43
<211> LENGTH: 10
<212> TYPE: PRT
<213> ORGANISM: Artificial Sequence

```
<220> FEATURE:
<223> OTHER INFORMATION: Description of Artificial Sequence: Fragment of
      human protein

<400> SEQUENCE: 43

Ser Ala Asp Val Glu Phe Cys Leu Ser Leu
 1               5                  10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 44

Thr Leu Glu Gly Phe Ala Ser Pro Leu Thr
 1               5                  10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 45

Cys Thr Asp Glu Tyr Met Gly Gly Gln His
 1               5                  10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 46

Asp Gly Thr Pro Glu Gly Pro Leu Arg Arg
 1               5                  10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 47

Phe Asn Asp Ile Asn Ile Tyr Asp Leu Phe
 1               5                  10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 48

Asn Gly Thr Pro Glu Gly Pro Leu Arg Arg
 1               5                  10
```

```
<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 49

Ser Met Asp Lys Ala Ala Asp Phe Ser Phe
  1               5                  10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 50

Ser Met Asp Lys Ala Ala Asn Phe Ser Phe
  1               5                  10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 51

Asp Val Glu Phe Cys Leu Ser Leu Thr Gln
  1               5                  10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 52

Ser Ser Asp Tyr Val Ile Pro Ile Gly Thr
  1               5                  10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 53

Asp Ile Asp Phe Ala His Glu Ala Pro Ala
  1               5                  10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein
```

```
<400> SEQUENCE: 54

Ser Asp Tyr Val Ile Pro Ile Gly Thr Tyr
 1               5                  10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 55

Asp Val Glu Phe Cys Leu Ser Leu Thr Gln Tyr
 1               5                  10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 56

Ile Tyr Asp Leu Phe Val Trp Met His Tyr Tyr
 1               5                  10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 57

Leu Thr Gly Asp Glu Asp Phe Thr Ile Pro Tyr
 1               5                  10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 58

Leu Thr Gly Asp Glu Asn Phe Thr Ile Pro Tyr
 1               5                  10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 59

Gln Ser Ser Met His Asn Ala Leu His Ile Tyr
 1               5                  10

<210> SEQ ID NO 60
<211> LENGTH: 11
<212> TYPE: PRT
```

```
<213> ORGANISM: Artificial Sequence
<220> FEATURE:
<223> OTHER INFORMATION: Description of Artificial Sequence: Fragment of
      human protein

<400> SEQUENCE: 60

Ser Ser Asp Tyr Val Ile Pro Ile Gly Thr Tyr
 1               5                  10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 61

Ser Thr Pro Met Phe Asn Asp Ile Asn Ile Tyr
 1               5                  10

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 62

Tyr Leu Glu Pro Gly Pro Val Thr Ala
 1               5

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 63

Gly Ser Thr Pro Met Phe Asn Asp Ile Asn Ile Tyr
 1               5                  10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 64

Ile Ser Ser Asp Tyr Val Ile Pro Ile Gly Thr Tyr
 1               5                  10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 65

Ser Gln Ser Ser Met His Asn Ala Leu His Ile Tyr
 1               5                  10
```

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 66

Met Leu Leu Ala Tyr Leu Tyr Cys Leu
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 67

Phe Ile Asp Ser Tyr Ile Cys Gln Val
 1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 68

His Leu Tyr Gln Cys Gln Val Val
 1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 69

Cys Leu Thr Ser Thr Val Leu Val
 1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Mutant

<400> SEQUENCE: 70

Lys Ala Asp Ile Cys Thr Asp Glu Tyr
 1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Mutant

<400> SEQUENCE: 71

```
Lys Cys Asp Ile Ala Thr Asp Glu Tyr
  1               5
```

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 72

```
Lys Ala Asp Ile Ala Thr Asp Glu Tyr
  1               5
```

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Mutant

<400> SEQUENCE: 73

```
Lys Ser Asp Ile Cys Thr Asp Glu Tyr
  1               5
```

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Mutant

<400> SEQUENCE: 74

```
Lys Cys Asp Ile Ser Thr Asp Glu Tyr
  1               5
```

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 75

```
Lys Ser Asp Ile Ser Thr Asp Glu Tyr
  1               5
```

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Mutant

<400> SEQUENCE: 76

```
Asp Ala Glu Lys Ala Asp Ile Cys Thr Asp Glu Tyr
  1               5                  10
```

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Mutant

```
<400> SEQUENCE: 77

Asp Ala Glu Lys Cys Asp Ile Ala Thr Asp Glu Tyr
  1               5                  10

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 78

Cys Leu Thr Ser Thr Val Gln Leu Val
  1               5

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Mutant

<400> SEQUENCE: 79

Asp Ala Glu Lys Ser Asp Ile Cys Thr Asp Glu Tyr
  1               5                  10

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 80

Ala Leu Leu Ala Val Gly Ala Thr Lys
  1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 81

Tyr Met Asp Gly Thr Asn Ser Gln Val
  1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 82

Lys Thr Trp Gly Gln Tyr Trp Gln Val
  1               5

<210> SEQ ID NO 83
<211> LENGTH: 9
<212> TYPE: PRT
<213> ORGANISM: Artificial Sequence
```

```
<220> FEATURE:
<223> OTHER INFORMATION: Description of Artificial Sequence: Fragment of
      human protein

<400> SEQUENCE: 83

Ile Thr Asp Gln Val Pro Phe Ser Val
 1               5

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 84

Val Leu Tyr Arg Tyr Gly Ser Phe Ser Val
 1               5                  10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 85

Leu Leu Asp Gly Thr Ala Thr Leu Arg Leu
 1               5                  10

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 86

Ala Ala Gly Ile Gly Ile Leu Thr Val
 1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 87

Ile Leu Thr Val Ile Leu Gly Val Leu
 1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 88

Glu Ala Asp Pro Thr Gly His Ser Tyr
 1               5
```

```
<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 89

Ser Ala Tyr Gly Glu Pro Arg Lys Leu
  1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 90

Glu Val Asp Pro Ile Gly His Leu Tyr
  1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 91

Phe Leu Trp Gly Pro Arg Ala Leu Val
  1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 92

Ala Ala Arg Ala Val Phe Leu Ala Leu
  1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 93

Tyr Arg Pro Arg Pro Arg Arg Tyr
  1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein
```

```
<400> SEQUENCE: 94

Lys Ile Phe Gly Ser Leu Ala Phe Leu
  1               5

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 95

Val Met Ala Gly Val Gly Ser Pro Tyr Val
  1               5                  10

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 96

Ile Ile Ser Ala Val Val Gly Ile Leu
  1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 97

Tyr Leu Ser Gly Ala Asn Leu Asn Leu
  1               5

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 98

Glu Ala Tyr Gly Leu Asp Phe Tyr Ile Leu
  1               5                  10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 99

Gln Asp Leu Thr Met Lys Tyr Gln Ile Phe
  1               5                  10

<210> SEQ ID NO 100
<211> LENGTH: 9
<212> TYPE: PRT
```

```
<213> ORGANISM: Artificial Sequence
<220> FEATURE:
<223> OTHER INFORMATION: Description of Artificial Sequence: Fragment of
      human protein

<400> SEQUENCE: 100

Glu Glu Lys Leu Ile Val Val Leu Phe
 1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 101

Ser Tyr Leu Asp Ser Gly Ile His Phe
 1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 102

Glu Glu Lys Leu Ser Val Val Leu Phe
 1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 103

Ser Tyr Leu Asp Ser Gly Ile His Ser
 1               5

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Fragment of
      human protein

<400> SEQUENCE: 104

Tyr Thr Asp Tyr Gly Gly Leu Ile Phe Asn Ser Tyr
 1               5                  10
```

CYSTEINE-DEPLETED PEPTIDES RECOGNIZED BY A3-RESTRICTED CYTOTOXIC LYMPHOCYTES, AND USES THEREFOR

This application claims priority under §119(e) from U.S. Ser. No. 60/037,781, filed Jan. 31, 1997, hereby incorporated by reference.

CROSS-REFERENCE TO RELATED APPLICATIONS

Ser. No. 60/027,627, filed Oct. 4, 1996, now pending, Ser. No. 60/013,972, filed Mar. 19, 1996, now pending, PCT/US95/01991, filed Feb. 16, 1995, Ser. No. 08/234,784, filed Apr. 29, 1994, now pending, Ser. No. 08/197,399 filed Feb. 16, 1994, now pending, are all hereby incorporated by reference in their entirety.

MENTION OF GOVERNMENT GRANT

Certain aspects of the invention may have been supported by NIH grants CA57653, AI21393, AI20963 and AI 33993. The U.S. Government may have certain rights in the invention.

BACKGROUND OF THE INVENTION

1. Field of the Invention

The present invention is directed to peptides that, in association with Class I MHC molecules, form epitopes recognized by cytotoxic T-cells specific for human diseases, to immunogens comprising said epitopic peptides, and to related compositions, methods and apparatus.

2. Description of the Background Art

There are two basic immune defenses in vertebrates. Humoral immunity is provided by antibodies, which defend primarily against bacterial, and the extracellular phase of viral, infections. Cellular immunity is provided by T cells, and their response is effective against microorganisms, parasites, cancer cells, foreign tissue (transplants), and both the intracellular and extracellular phase of viral infections. The cytotoxic T cell (lymphocyte) is a particular class of cellular immune response effector cell which eliminates invaders directly, e.g., by lysis. The two systems of cellular immunity interact in complex ways.

The present invention therefore contemplates the inhibition of diseases caused by viruses, bacteria, fungi, protozoa, algai, and other microorganisms, by multicellular parasites, and by cancer cells.

The prevention and treatment of cancer, and especially of melanoma, is of particular interest.

Melanoma affects 30,000 new patients per year in the United States. It is a cancer manifested by the unabated proliferation of melanocytes. Eighty percent of melanoma patients are diagnosed during their productive years between the ages of 25 and 65. The incidence of melanoma is rapidly increasing, in 1935 the lifetime risk of developing melanoma was 1:1,500 individuals, at present, the risk has risen to 1:105. It is believed that by the year 2000 the risk of developing melanoma will increase to about 1:70 to 1:90. Early diagnosis and treatment of this disease is crucial. Once a primary tumor becomes metastatic the disease is almost always fatal.

Cytotoxic lymphocyte (CTL) response has been shown to be an important host defense against malignant cells, Rock et al. J. Immunol., (1993), 150:1244.

Lymphocytes isolated from patients having melanoma, when stimulated in vitro with recombinant interleukin-2 (rIL-2) and autologous melanoma cells, develop a melanoma specific cytotoxic response, Vose et al., Nature, (1982), 296:359; Knuth et al., Proc. Natl. Acad. USA, (1984), 81:3511; Slingluff et al., Arch. Surg., (1987), 122:1407; Darrow et al., Cancer, (1988), 62:84; Slingluff et al., J. Natl. Cancer Inst., (1988), 80:1016; Slingluff et al., Ann. Surg., (1989), 210:194; Muul et al., J. Immunol., (1987), 138:989; Van den Eynde et al., Int. J. Cancer, (1989), 44:634; Anichini et al., Int. J. Cancer, (1985), 35:683. The majority of melanoma-specific effector lymphocytes are $CD8^+$ cytotoxic T lymphocytes (CTL) that are restricted by class I Major Histocompatibility Complex (MHC) molecules, Vose et al; Slingluff et al (1988), supra, Hersey et al., Cancer Immunol. Immunother., (1986), 22:15. These characteristics are resent whether CTL have been generated from peripheral blood lymphocytes (PBL), lymph node cells, or tumor infiltrating lymphocytes.

The evidence that the CTL response to human melanoma is restricted by class I MHC molecules includes demonstration of cross-reactivity for allogenic melanoma cells that share a restricting class I MHC molecule with the autologous tumor. The HLA-A2 molecule and its variants, of which HLA-A2.1 is by far the most common, is an effective restricting element for the melanoma-specific CTL response. Additionally, melanoma-specific HLA-restricted CTL lyse the majority of $A2^+$ melanomas tested, Darrow et al., J. Immunol., (1989), 142:3329; Wolfel et al., J. Exp. Med., (1989), 170:797; Hom et al., J. Immunother., (1991), 3:153. By demonstrating lysis of A2-melanomas transfected with the A2.1 gene, it has been shown that these transfected melanomas can present the epitopes recognized by A2-restricted melanoma-specific CTL, Kawakami et al., J. Immunol., (1992), 148:638. These results suggest that these CTL recognize A2-restricted epitopes that are shared by the majority of melanomas, although very little is known about the number and identity of their epitopes.

Class I molecules of the Major Histocompatibility Complex (MHC) bind to peptides derived from intracellular pathogens or from proteins expressed in tumor cells, and present them on the cell surface to the host immune system. The mechanism of peptide presentation involves protein synthesis and proteolysis in the cytosol, followed by transport of peptides into the endoplasmic reticulum (ER), through the action of the TAP transporter molecules. Peptides then become associated with newly synthesized class 1 molecules, and the resulting complexes move to the cell surface. Proteins that are membrane associated or secreted contain signal sequences that cause them to be contranslationally transferred into the ER from membrane-bound ribosomes. Such proteins would thus be protected from the action of cytoplasmic proteases. However, since peptide epitopes do arise from such proteins, although their TAP dependent expression is unclear, it has been assumed that the proteolysis to generate these peptide epitopes occurs after these proteins have been aberrantly translated on cytoplasmic ribosomes.

Adoptive transfer of tumor stimulated CTL has been associated with some tumor regressions, Rosenberg et al., N. Eng. J. Med., (1988), 319:1676.

An alternate approach to augmenting the T-cell response to melanoma is the use of a vaccine to stimulate CTL in vivo (active specific immunotherapy). Epitopes for $CD8^+$ CTL are believed to be short, usually 9-residue peptides that bind to a cleft on the surface of the class I MHC molecule, Udaka et al., Cell, (1992), 69:989; VanBleek et al., Nature, (1990), 348:213; Falk et al., J. Exp. Med., (1991), 174:425. These peptides, generated from proteolysis of endogenous proteins in the cytosol, are transported to the endoplasmic reticulum, where they become associated with newly synthesized class I MHC molecules. They are then transported to the cell surface, Elliott et al., Nature, (1990), 3348:195. CTL epitopes have been reconstituted in vitro by allowing exogenous peptides to bind to MHC molecules on the cell surface of target cells, Townsend et al., Annu. Rev. Immunol., (1989), 7:601.

Several CTL epitopes have been identified which comprise cysteine, e.g., MLLAYLYCL (SEQ ID NO:66) (see Table A and Boon, et al., Eur. J. Immunol., 24:759–64 (1994)). However, prior to the priority application, it had not been suggested that it could be advantageous to replace these cysteines with non-cysteine residues. Indeed, there would have been concern that such replacement would adversely effect the interaction of the epitope with the class I MHC molecule or with the T cell receptor, or the specificity of the response to the epitope.

Meadows, et al., Immunity, 6:273–81 (1997), published after the priority date, discloses a nine residue H-Y specific CTL epitope FIDSYICQV (SEQ ID NO:67). It was discovered that cysteinylation of the cysteine affected recognition, improving recognition by one clone, and reducing recognition by another.

DiModugno, et al, J. Immunother., 20:431–6 (1997), published after the priority date, characterized certain cysteine-containing CTL epitopes (HLYQCQVV (SEQ ID NO:68) and CLTSTVLV (SEQ ID NO:69)) of the HER-2/neu gene product. DiModugno made Ser and Ala substitution mutants of CLTSTVLV (SEQ ID NO:69) to prevent dimenzation; there was no effect, good or bad, on the binding of the peptide to high affinity HLA-A2.1 molecules, and hence no motivation to perform such substitutions on other epitopes in the future.

SUMMARY OF THE INVENTION

The present invention is particularly directed to "cysteine-depleted" CTL epitopes, in which one or more cysteines not essential to eliciting the desired CTL response are replaced by another amino acid, especially Ala, Thr, Ser or Gly.

The present invention relates to immunogens which are capable of eliciting a disease-specific cytotoxic lymphocyte response in at least some individuals, which response is directed to peptide epitopes carried by those immunogens, and to the use of those immunogens in active specific immunotherapy and immunoprophylaxis against that disease. Melanoma is of particular interest.

These immunogens may be used as vaccines, in active specific immunotherapy. The immunogens may be administered directly or by gene therapy. The epitopic peptides may also be used to stimulate lymphocytes, the latter then being used for adoptive immunotherapy.

An antigen associated with a particular disease may elicit a CTL response, in which case the antigen must be processed into peptide fragments which are CTL epitopes. In some instances these native CTL epitope contains cysteine. If so, it is possible that intermolecular disulfide bonds will form between cysteines of two different epitopic peptides. If the epitope contains two or more cysteines, it is possible to form intramolecular disulfide bonds, too. Applicants have discovered that such disulfide bond formation can interfere with the CTL response.

One may reduce the total Cys to one, thus preventing intramolecular disulfide bond formation, or to zero, thereby also blocking intermolecular disulfide bonding.

In a preferred embodiment, the native CTL epitope is one other than DiModugno's CLTSTVQLV (SEQ ID NO:78), which is a CTL epitope of a breast and ovarian tumor-associated antigen.

In other preferred embodiments, the cysteine depletion is applied to a cysteine-incorporating CTL epitope of the melanoma-associated antigens pMel-17 or tyrosinase.

A native tyrosinase CTL epitope of particular interest is the peptide Lys-Cys-Asp-Ile-Cys-Thr-Asp-Glu-Tyr (SEQ ID NO:19). We have discovered that substitution of Ser or Ala for Cys-2 in peptide KCDICTDEY (SEQ ID NO:19) increases the ability to reconstitute the epitope in vitro, probably by prevention of intramolecular disulfide bonds. The same principles apply to the related EKCDICTDEY (SEQ ID NO:37) and DAEKCDICTDEY (SEQ ID NO:10) sequences, and indeed to any Cys-containing CTL epitopes.

Additional embodiments of the present invention are described below. References to melanoma should be deemed to apply, *mutatis mutandis*, to other diseases, too.

BRIEF DESCRIPTION OF THE DRAWINGS

FIGS. 1A–B. Recognition of autologous and HLA-matched melanomas by melanoma-reactive CTL. In 1A), VMM12 CTL are evaluated for lysis of a panel of target cells. The VMM12 CTL recognize shared melanoma antigens presented by HLA-A1 (VMM15 melanoma cells share HLA-A1 with VMM12), and by HLA-A3 (VMM10 melanoma cells share HLA-A3 with VMM12). Similarly, in 1B), VMM15 CTL are evaluated in the same manner. VMM15 CTL recognize shared melanoma antigens presented by HLA-A1 (VMM12 melanoma cells) and by either HLA-A1, -A25, or -B8 (VMM14 melanoma cells).

FIGS. 2A–B. HLA-A1+ CTL lines recognize tyrosinase peptides on HLA-A1. In 2A), VMM12 CTL are capable of lysing C1R-A1 cells infected with a vaccinia-tyrosinase construct. In 2B), VMM15 CTL also recognize tyrosinase.

FIG. 3. VMM15 CTL recognize Peptides containing KCDICTDEY (SEQ ID NO:19) in association with HLA-A1. C1R-A1 cells were pulsed with 10 uM, 1 uM and 0.1 uM concentrations of synthetic peptides prior to addition of VMM15 CTL. Background lysis of C1R was approximately 10%. Direct cytotoxicity by the peptides themselves was negligible (open diamonds), averaging 0–2%. An epitope for VMM15 CTL was reconstituted by three of the test peptides, numbers 5, 12, and 15, corresponding to KCDICTDEY (SEQ ID NO:19), DAEKCDICTDEY (SEQ ID NO:10), and EKCDICTDEY (SEQ ID NO:37) as marked.

FIG. 4. VMM12 CTL recognize a peptide containing KCDICTDEY (SEQ ID NO:19) in association with HLA-A1. C1R-A1 cells were pulsed with peptides (SEQ ID NOS:2–17, the sequence identifiers having been applied to the sequences as listed from top to bottom) at 1 to 0.01 $\mu$M concentrations prior to adding VMM12 CTL. The peptides themselves were not cytolytic (open diamonds). The peptide DAEKCDICTDEY (SEQ ID NO:10) reconstituted an epitope for these VMM12 CTL, although weakly.

FIG. 5. Amino acid sequence (SEQ ID NO:1) of tyrosinase, with the Position of KCDICTDEY (SEQ ID NO:19) highlighted and underlined. The high proportion of cysteine residues and acidic residues are noted relative to the proportion in the intact protein.

FIG. 6. Synthetic peptides from the tyrosinase protein were tested for recognition bv HLA-A1-restricted VMM15 CTL. C1R cells were labeled with $^{51}Cr$ and pulsed with the indicated crude synthetic peptides (SEQ ID NOS:18–61, 10 and 63–65, the sequence identifiers having been applied to the sequences as listed from top to bottom) at approximately 20 micrograms/ml for 2 hours prior to CTL co-culture. CTL were used at an E:T of 15:1. Open bars indicate lysis in the presence of CTL. As a control for possible direct peptide toxicity, lysis was also measured in the absence of CTL (filled bars). Reconstitution of the CTL epitope was observed for three peptides: KCDICTDEY (SEQ ID NO:19), EKCDICTDEY (SEQ ID NO:37), and DAEKCDICTDEY (SEQ ID NO:10), with 25–40% target cell lysis for those three peptides, and with 10% background lysis of target cells pulsed with irrelevant peptides.

Figure 7:
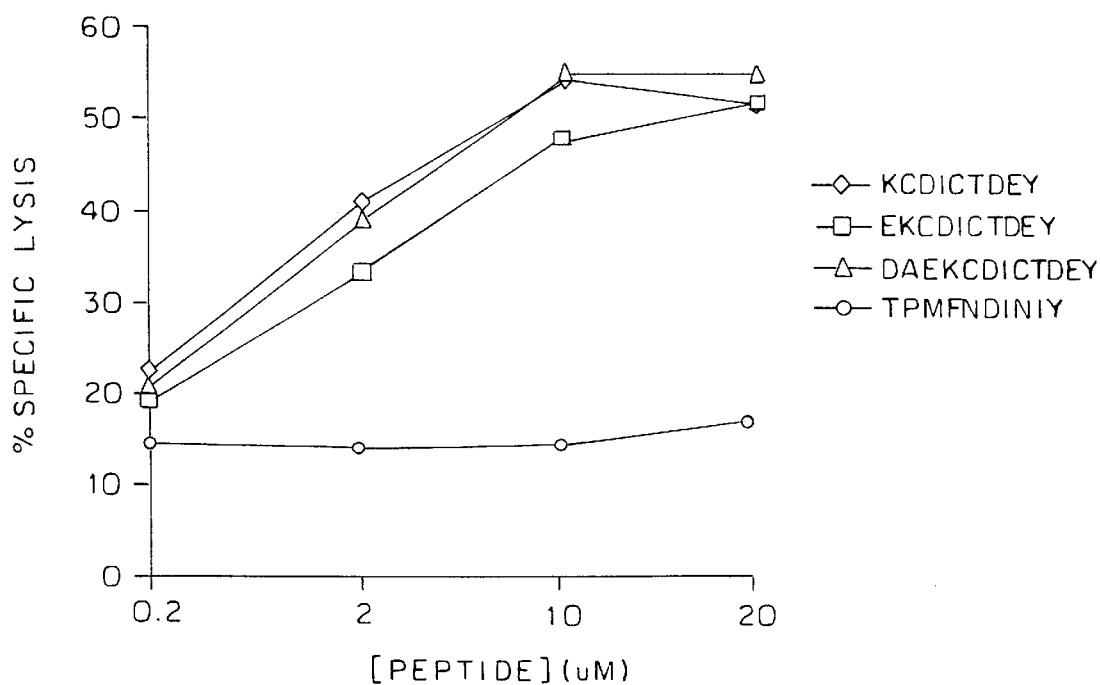

FIG. 7. VMM15 CTL recognize, at comparable doses, 9-, 10- and 12-residue peptides containing the amino acid sequence KCDICTDEY (SEQ ID NO:19) in association with HLA-A1.

These three synthetic peptides were purified by HPLC, and evaluated in a dose-titration assay. C1R transfectants expressing HLA-A1 (C1R-A1) were labeled with $^{51}$Cr and then pulsed with the indicated peptides at various concentrations (abcissa) for 2 hours prior to CTL co-culture. Cytotoxicity was measured in a standard chromium release assay. Recognition of C1R-A1 cells pulsed with each of these KCDICTDEY (SEQ ID NO:19)-containing peptides was similar and, at the higher concentrations, lysis of these peptide pulsed targets equalled lysis of the autologous VMM15 melanoma cells. TPMFNDINIY (SEQ ID NO:39) is an irrelevant peptide derived from tyrosinase that also fits the HLA-A1 binding motif. Lysis of non-peptide pulsed C1R cells was 19%, and lysis of VMM15 tumor cells (positive control) was 50%. An effector:target ratio of 25:1 was used.

Figure 8A:
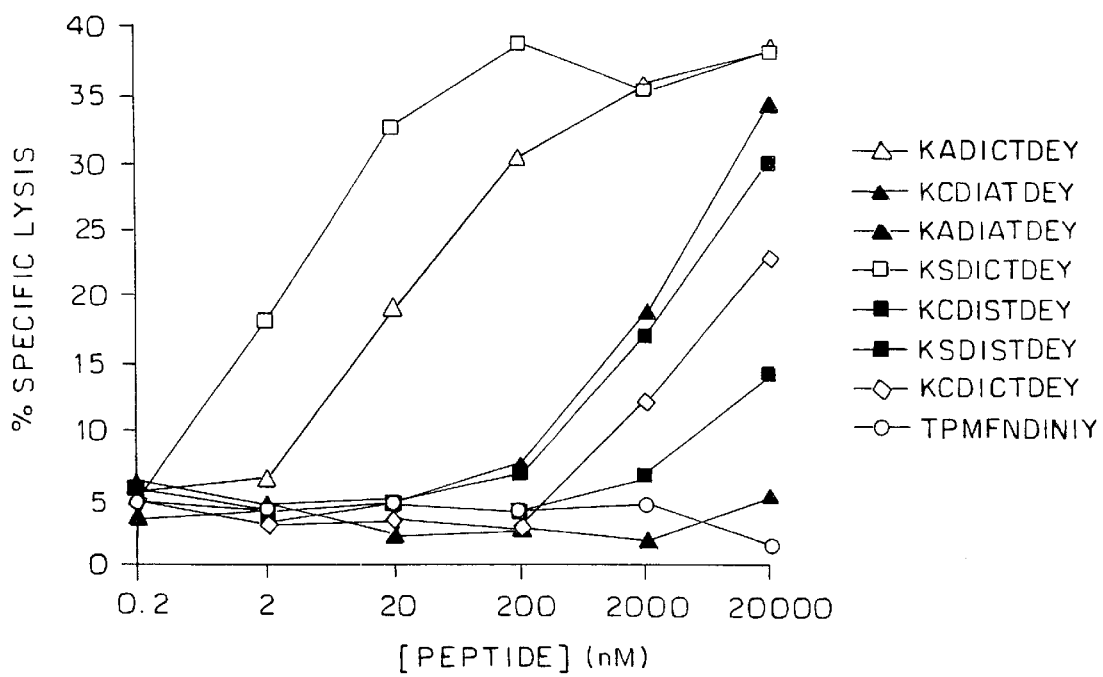
Figure 8B:
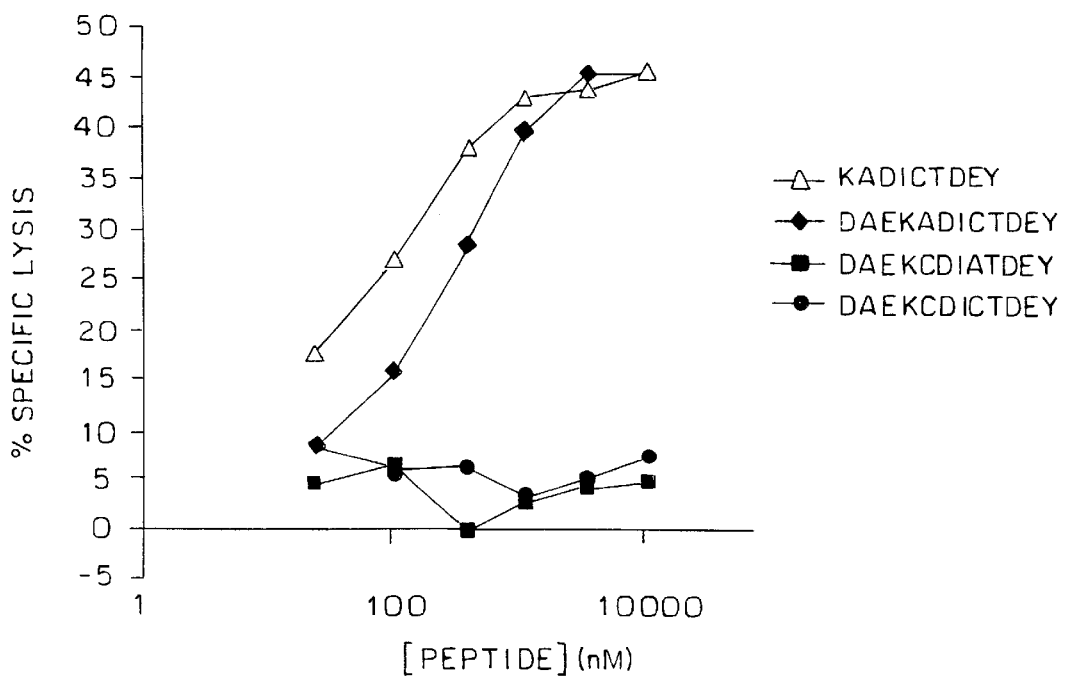

FIG. 8: Alanine or serine substitution at the more aminoterminal cysteine greatly enhances VMM15 CTL recognition. CTL recognition of alanine and serine substitued peptides. C1R transfectants expressing HLA-A1 (C1R-A1) were labeled with $^{51}$Cr and then pulsed with the indicated peptides at various concentrations (abcissa) for 2 hours prior to CTL co-culture, at which time the peptide concentration dropped 2-fold. TPMFNDINIY (SEQ ID NO:39) is derived from tyrosinase and fits the HLA-A1 binding motif. Cytotoxicity was measured in a stardard chromium release assay. In A, VMM15 CTL were used at an E:T of 25:1. Lysis of autologous tumor was 44%, lysis of non-peptide pulsed C1R-A1 was 3%. In B, VMM15 CTL were used at an E:T of 10:1. Lysis of autologous tumor was 70%, and lysis of non-peptide pulsed C1R-A1 was 4%.

Figure 9:
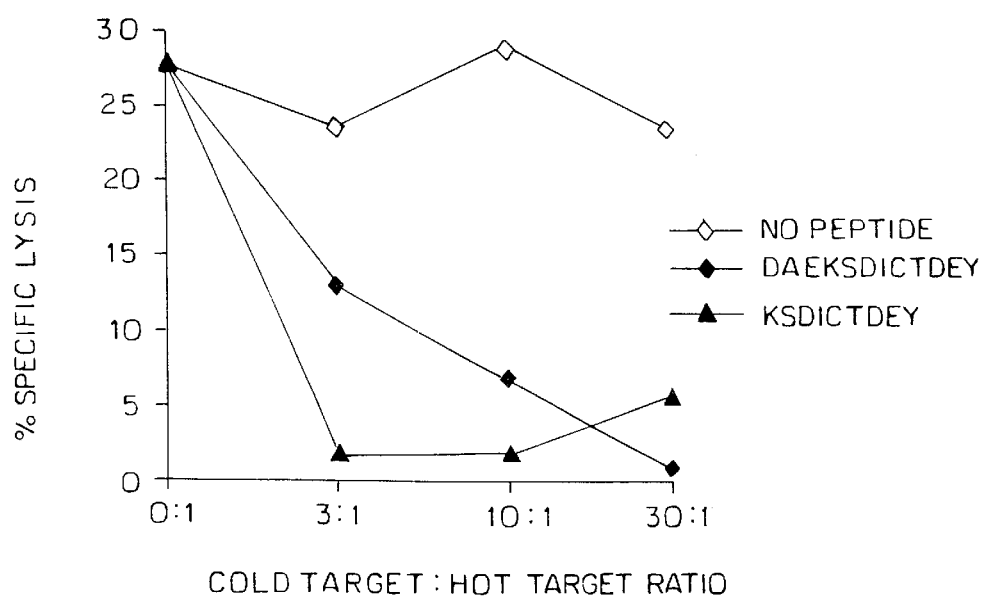

FIG. 9. The dodecamer peptide DAEKSDICTDEY (SEQ ID NO:79) competes with the nonamer peptide KSDICTDEY (SEQ ID NO:73) for recognition by VMM15 CTL. B-LCL derived from patient VMM15 (VMM15 EBV) were $^{51}$Cr-labeled, pulsed with the peptide KSDICTDEY (SEQ ID NO:73) at a final concentration of 20 µg/ml for 1 hour, then washed. Unlabeled (cold) VMM15 EBV were similarly treated with KSDICTDEY (SEQ ID NO:73), DAEKSDICTDEY (SEQ ID NO:79), or no peptide, as indicated. Increasing numbers of these various unlabeled targets were pre-incubated with VMM15 CTL for 1 hour at 37° C. Labeled (hot) targets were then added for an additional 4 hour co-culture at a final effector-to-labeled target ratio of 10:1.

DETAILED DESCRIPTION OF THE PREFERRED EMBODIMENTS OF THE INVENTION

The present invention relates to certain melanomaspecific CTL epitopes, and their incorporation into immunogens for immunoprophylactic and immunotherapeutic purposes.

CTL Epitopes

An epitope may be said to be associated with a particular infectious disease if it is presented by an intracellular, surface, or secreted antigen of the organism which causes the disease, or in the case of a virus, if it is associated with viral particles or is specific to a cell infected by the virus.

It may be said to be associated with a particular tumor if it is presented by an intracellular, surface or secreted antigen of said tumor. It need not be presented by all cell lines of the tumor type in question, or by all cells of a particular tumor, or throughout the entire life of the tumor. It need not be specific to the tumor in question. An epitope may be said to be "tumor associated" in general if it is so associated with any tumor.

The term "disease associated epitope" also includes any non-naturally occurring epitope which is sufficiently similar to an epitope naturally associated with the disease in question so that cytotoxic lymphocytes which recognize the natural disease epitope also recognize the similar non-natural epitope.

An epitope may be said to be specific to a particular source (such as a disease-causing organism or a tumor), if it is associated more frequently with that source than with other sources. Absolute specificity is not required, provided that a useful prophylactic, therapeutic or diagnostic effect is still obtained.

In the case of a "tumor-specific" epitope, it more frequently associated with that tumor that with other tumors, or with normal cells. Preferably, there should be a statistically significant (p=0.05) difference between its frequency of occurrence in association with the tumor in question, and its frequency of occurrence in association with (a) normal cells of the type from which the tumor is derived, and (b) at least one other type of tumor. An epitope may be said to be "tumor-specific" in general is it is associated ore frequently with tumors (of any or all types) than with normal cells. It need not be associated with all tumors.

The term "tumor specific epitope" also includes any non-naturally occurring epitope which is sufficiently similar to a naturally occurring epitope specific to the tumor in question (or as appropriate, specific to tumors in general) so that cytotoxic lymphocytes stimulated by the similar epitope will be essentially as specific as CTLs stimulated by the natural epitope.

In general, tumor-versus-normal specificity is more important than tumor-versus-tumor specificity as (depending on the route of administration and the particular normal tissue affected), higher specificity generally leads to fewer adverse effects. Tumor-versus-tumor specificity is more important in diagnostic as opposed to therapeutic uses.

The reference to an epitope as being "restricted" by a particular allele of MHC, such as HLA-A1, indicates that such epitope is bound and presented by the allelic form in question. It does not mean that said epitope might not also be bound and presented by a different allelic form of MHC, such as HLA-A2, HLA-A3, HLA-B7, or HLA-B44.

The disease-specific CTL epitopes of the present invention are peptides, typically 9–13 amino acids in length, which are sufficiently similar to a disease-specific epitope recognized by a disease-specific CTL to be useful, under suitable conditions of use, to protect an individual from that disease, or to be useful in the diagnosis of the disease or of a patient's ability to fight the disease by a CTL response. Preferably, these epitopes are substantially identical with disease CTL peptide epitopes of naturally occurring antigens associated with the disease recognized by disease-specific CTLs. For the purpose of the present invention, a melanoma-specific CTL epitope is an epitope which is recognized by a T-cell receptor of at least some cytotoxic lymphocytes of at least some individuals in the population of interest, and which is more frequently or strongly associated with melanoma cells than with at least some other cancer and/or normal cells. There may be some cross-reactivity, for example, with other cells of melanocytic lineage. Absolute specificity is not required, provided that a useful prophylactic, therapeutic or diagnostic effect is still obtained.

A cysteine-depleted epitope is one which differs from a native CTL epitope in that at least one cysteine residue of the native epitope is replaced by a non-cysteine residue. By definition, a cysteine-depleted epitope is not identical to a native CTL epitope. However, a cysteine-depleted epitope could be used in conjunction with the corresponding native epitope, with a different native CTL epitope which does not contain cysteine, a different native CTL epitope which does contain cysteine, with a non-native CTL epitope which may or may not contain cysteine, or with another cysteine-depleted form of the same or a different native CTL epitope.

Melanoma-specific CTL epitopes which are identical to or otherwise substantially homologous with a pMel-17 or tyrosinase CTL eptiope are of particular interest. The cysteine-depleted mutant of (DAE) KCDICTDEY (SEQ ID NO:10) (A1-restricted) could be used by itself or in conjunction with other epitopes, such as the pMel-17 epitopes YLEPGPVTA (SEQ ID NO:62) (Peptide 946L) (A2.1-restricted) and ALLAVGATK (SEQ ID NO:80) (A3-restricted), and the tyrosinase epitope YMDGTNSQV (SEQ ID NO:81) (peptide 1030) (A2.1-restricted). The "(DAE)" indicates optionally included residues (or equivalents).

The family of melanoma epitopes which are recoverable from an individual is dependent on the nature of the binding site of the Class I MHC (HLA) molecules expressed by the individual, and, as a result of the polymorphism of the Class I MHC (HLA) molecules, can vary considerably from one individual to another. For the purpose of the present invention, the melanoma cell line used as a source of melanoma-specific CTL epitopes may be any melanoma cell line; similarly, the Class I MHC (HLA) molecule may be any such molecule borne by a melanoma which is capable of binding to and presenting a melanoma-specific epitope, including, but not limited to, the various allelic forms of Class I MHC molecules, including but not limited to those enumerated in Table I. Among the Class I molecules, the principal genetic loci are denoted as HLA-A, HLA-B, and HLA-C. The preferred epitopic sequence may vary depending on the restriction system.

Application of active specific immunotherapy to a heterogeneous melanoma patient population would be facilitated by identification of CTL epitopes presented in association with a wide range of class I MHC molecules. Besides HLA-A2, the most commonly expressed class I MHC molecules are A1 and A3, then B7 and B8. Approximately 90% of the melanoma patient population should express one or more of these molecules or HLA-A2. Peptides from MAGE-1 and MAGE-3 have been identified as HLA-A1-restricted CTL epitopes, and a few peptides have been identified for some of the less common MHC molecules, including A24, A31, and B44. Little work has been done toward identification of HLA-A3-restricted responses, and—except for the peptides from MAGE proteins—little work has been done toward identification of HLA-A1-restricted responses.

Preferably, the epitope is one restricted by one of the more prevalent forms (in the melanoma patient population) of these loci. The loci HLA-A1, HLA-A2, HLA-A3, HLA-B7 and HLA-B8 are of greatest interest. Within HLA-A2, HLA-A2.1 is of particular interest. However, over half of patients do not express HLA-A2.1, and it is therefore desirable to identify immunodominant CTL peptide epitopes restricted by common MHC molecules other than HLA-A2.1, e.g., HLA-A1.

Preferably, the CTL epitopes of the present invention, in the cytotoxicity assay described hereafter, when used in oligopeptide form to reconstitute epitopes for suitable CTL, achieve, at the dosage resulting in maximal lysis of target cells exposed to the stimulated CTL, a percentage lysis of target cells which is at least 10 percentage points higher (more preferably, at least 20 points higher) the background level of lysis of the target cells by the CTLs (i.e., in absence of the peptide).

Generally speaking, in addition to epitopes which are identical to the naturally occurring disease-specific epitopes, the present invention embraces epitopes which are substantially identical with such epitopes, and therefore disease-specific in their own right.

The term "substantially identical", when used in connection with amino acid sequences, refers to sequences which are substantially identical to or similar in sequence with each other, giving rise to a homology in conformation and thus to similar (or improved) biological activity. The term is not intended to imply a common evolution of the sequences.

An epitope is considered substantially identical to a reference epitope if it has at least 10% of an immunological activity of the reference epitope and differs from the reference epitope by no more than one non-conservative substitution not suggested by a known binding motif of the pertinent MHC molecule. Any number of highly conservative, conservative or semi-conservative substitutions, or non-conservative substitutions suggested by known binding motifs, subject to the activity limitation, are permitted.

Kast, et al., J. Immunol, 152:3904–12 (1994) sets forth HLA-A specific peptide binding motifs for the HLA molecules A1, A2.1, A3, A11 and A24. Engelhard, et al., in Sette, ed., Naturally Processed Peptides, 57:39–62 (1993) explored the features that determined binding to HLA-A2.1 and HLA-B7. See also Hobohim et al; Eur. J. Immunol., 23:1271–6 (1993); Kawakami, et al., J. Immunol., 154:3961–8 (1995). Based on these and other sources, the preferred and tolerated AAs for various HLA molecules include (but are not limited to) the following:

TABLE 10

| Molecule | Position | Preferred AA | tolerated AA |
| --- | --- | --- | --- |
| A1 | 2 | T, S, M | |
| | 3 | D, E | A, S |
| | 9 | Y | |
| A2.1 | 2 | L, M | I, V, A, T |
| | 9 | L, V, I | A, M, T |
| A3 | 2 | L, M, I, V, S A, T, F | C, G, D |
| | 9 | K, R, Y, H, F | A |
| A11 | 2 | M, L, I, V, S A, T, G, N | C, D, F |
| | 9 | K | R, H, Y |
| A24 | 2 | Y, F, W | M |
| | 9 | F, L, I, W | |
| B7 | 1 | A | M, S, R, L |
| | 2 | P | V |
| | 3 | R | A, K, S, M |
| | 9 | L | I, A, V |

TABLE 10-continued

| Molecule | Position | Preferred AA | tolerated AA |
|---|---|---|---|
| B8 | 3 | K | not known |
|  | 5 | K | not known |
|  | 9 | L | not known |
| B27 | 2 | R | not known |
|  | 9 | R, K, H | not known |
| B35 | 2 | P | not known |
|  | 9 | Y | not known |
| B53 | 2 | P | not known |

If a position is not listed, studies revealed a greater variability of AAs than for the listed positions. For listed positions, AAs not listed may be tolerated, especially if they are conservative or semi-conservative substitutions for "preferred" or "tolerated" AAs.

Substantially identical peptide epitopes may be identified by a variety of techniques, some of which do not depend on preexisting knowledge of the binding motif. Thus, it is known in the art that one may synthesize all possible single substitution mutants of a known peptide epitope. For a nonpeptide, there are (20×9−1=179) such mutants. Geysen, et al., Proc Nat. Acad. Sci. (USA), 81:3998–4002 (1984). While the effects of different substitutions are not always additive, it is reasonable to expect that two favorable or neutral single substitutions at different residue positions in the epitope can safely be combined in most cases.

One may also synthesize a family of related single or multiple substitution mutants, present the mixture to the HLA-A2.1 positive lymphoblastoid cell line T2 (or other cell line capable of presenting melanoma-specific CTL epitopes), and expose the T2 cells to melanoma-specific CTLs. If the T2 cells are lysed, the effective epitopes may be identified either by direct recovery from the T2 cells or by a progressive process of testing subsets of the effective peptide mixtures. Methods for the preparation of degenerate peptides are described in Rutter, U.S. Pat. No. 5,010,175, Haughten, et al., Proc. Nat. Acad. Sci. (USA), 82:5131–35 (1985), Geysen, et al., Proc. Nat. Acad. Sci. (USA), 81:3998–4002 (1984); WO86/06487; WO86/00991.

Multiple mutagenesis may be used to screen a few residue positions intensely or a larger number of positions more diffusely. One approach is to explore at least a representative member of each a.a. type at each position, e.g., one representative of each of exchange groups I–V as hereafter defined. Preferably, Gly and Pro are screened in addition to one other group I residue. Preferably, at least one screened residue is an H-bonding residue. If a positive mutant features a particular representative, like amino acids can be explored in a subsequent library. If, for example, a Phe substitution improves binding, Tyr and Trp can be examined in the next round.

For one preferred A1 peptide a possible multiple mutagenesis strategy would be

| Lys | Cys | Asp | Ile | Cys | Thr | Asp | Glu | Tyr |
|---|---|---|---|---|---|---|---|---|
| Arg | Thr | Glu | Leu | Thr | Ala | Glu | Asp | Phe |
| His | Ser |  | Val | Ser | Ser |  |  | Trp |
|  | Ala |  | Met | Ala | Pro |  |  |  |
|  | Met |  |  | Gly | Gly |  |  |  |
|  | Gly |  |  | Met |  |  |  |  |

These strategies take into account conservative substitutions for the wild type AAs, and the known A1, A2.1 and A3 binding motifs, and preferred method of cysteine depletion.

The person of ordinary skill in the art, in determining which residues to vary, may also make comparisons of the sequences of the naturally processed MHC associated peptides, and may obtain 3D structures of the MHC: peptide: TCR complexes, in order to identify residues involved in MHC or TCR binding. Such residues may either be left alone, or judiciously mutated in an attempt to enhance MHC or TCR binding.

It is also possible to predict substantially homologous epitopes by taking into account studies of sequence variations in families of naturally occurring homologous proteins. Certain amino acid substitutions are more often tolerated than others, and these are often correlatable with similarities in size, charge, etc. between the original amino acid and its replacement. Insertions or deletions of amino acids may also be made. N- and C-terminal truncations or extensions are more likely to be tolerated than internal deletions or insertions. With regard to truncation, the peptide may be truncated by one or more amino acids and still be substantially homologous, however, it cannot be fewer than five amino acids. Extensions are permissible, however, note that larger peptides are digested in vivo prior to presentation.

Conservative substitutions may be made in the amino acid sequence of the proteins of interest without compromising the desired properties of the peptides, i.e., induction of cytotoxic T-lymphocytes in a patient when administered thereto.

Conservative substitutions are herein defined as exchanges within one of the following five groups:

I. Small aliphatic, nonpolar or slightly polar residues: Ala, Ser, Thr, Pro, Gly II. Polar, negatively charged residues: and their amides Asp, Asn, Glu, Gln III. Polar, positively charged residues: His, Arg, Lys IV. Large, aliphatic, nonpolar residues: Met, Leu, Ile, Val, Cys V. Large, aromatic residues: Phe, Tyr, Trp Within the foregoing groups, the following substitutions are considered "highly conservative":

Asp/Glu

His/Arg/Lys

Phe/Tyr/Trp

Met/Leu/Ile/Val

Semi-conservative substitutions are defined to be exchanges between two of groups (I)–(V) above which are limited to supergroup (A), comprising (I), (II) and (III) above, or to supergroup (B), comprising (IV) and (V) above. Also, Ala is considered a semi-conservative substitution for all non group I amino acids.

It will be appreciated that highly conservative substitutions are less likely to affect activity than other conservative substitutions, conservative substitutions are less likely to affect activity than merely semi-conservative substitutions, and semi-conservative substitutions less so than non-conservative substitutions.

Although a substitution mutant, either single or multiple, of the peptides of interest may not have quite the potency of the original peptide, such a mutant may well be useful.

Substitutions are not limited to the genetically encoded, or even the naturally occurring amino acids. When the epitope is prepared by peptide synthesis, the desired amino acid may be used directly. Alternatively, a genetically encoded amino acid may be modified by reacting it with an organic derivatizing agent that is capable of reacting with selected side chains or terminal residues. The following examples of chemical derivatives are provided by way of illustration and not by way of limitation.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole-(alkyl)alanines, and D- or L-alkylainines where alkyl may be substituted or unsubstituted methyl, ethyl, propyl, hexyl, butyl, pentyl, iso-propyl, iso-butyl, sec-isotyl, iso-pentyl, non-acidic amino acids, of C1–C20.

Acidic amino acids can be substituted with non-carboxylate amino acids while maintaining a negative charge, and derivatives or analogs thereof, such as the non-limiting examples of (phosphono)-alanine, glycine, leucine, isoleucine, threonine, or serine; or sulfated (e.g., —$SO_3H$) threonine, serine, tyrosine.

Other substitutions may include unnatural hyroxylated amino acids made by combining "alkyl" (as defined and exemplified herein) with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage can be replaced by a ketomethylene moiety, e.g. (—C(=O)—$CH_2$—) for (—(C=O)—NH—). Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

In addition, any amino acid can be replaced by the same amino acid but of the opposite chirality. Thus, any amino acid naturally occurring in the L-configuration (which may also be referred to as the R or S configuration, depending upon the structure of the chemical entity) may be replaced with an amino acid of the same chemical structural type, but of the opposite chirality, generally referred to as the D-amino acid but which can additionally be referred to as the R— or the S—, depending upon its composition and chemical configuration. Such derivatives have the property of greatly increased stability to degradation by enzymes, and therefore are advantageous in the formulation of compounds which may have longer in vivo half lives, when administered by oral, intravenous, intramuscular, intraperitoneal, topical, rectal, intraocular, or other routes.

The thiol group of cysteine reacts very rapidly with alkyl halides, such as iodoacetate, iodoacetamide, methyl iodine, and so on, to give the corresponding stable alkyl (substituted or unsubstituted) derivatives, such as —$CH_2$—S—$CH_3$. The thiol group can also add across double bonds such as those of N-ethylmaleimide or of maleic anhydride, and it can open the ring of ethyleneimine, providing a new site for tryptic cleavage. Thiols form complexes with various metal (especially mercury, silver, arsenic, copper, iron, zinc, cobalt, molybdenum, manganese and cadmium ions) and organometal ions (e.g., R—$Hg^+$, such as para-mercuribenzoic acid).

The thiol group may be oxidized to yield a disulfide bond or a sulfonate. A thiol may be converted to a disulfide by thiol-disulfide exchange, for example, exchange with an aromatic disulfide such as dithionitrobenzoic acid (DTNB) or Ellman's reagnet. Of course, a cysteine residue may be disulfide bonded to a cysteine residue in the same or a different peptide, or to a free cysteine. By way of further examples, some of which are already embraced by the general discussion above, cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)-propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1 M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—I—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be readily deamidated to the corresponding glutamyl and aspartyl residues. Alternatively, these residues may be deamidated under mildly acidic conditions. Either form of these residues falls within the scope of the present invention.

Derivatization with bifunctional agents is useful for cross-linking the peptide to a water-insoluble support matrix or to other macromolecular carriers, according to known method steps. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 (which are herein incorporated entirely by reference), may be employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., *Proteins: Structure and Molecule Properties*, W. H. Freeman & Co., San Francisco, pp. 79–86 (1983)), acetylation of the N-terminal amine, methylation of main chain amide residues (or substitution with N-methyl amino acids) and, in some instances, amidation of the C-terminal carboxyl groups, according to known method steps. Glycosylation is also possible.

Derivatized moieties may impart altered affinity for their target, altered immunogenicity, or improved solubility, absorption, biological half life, and the like, or attenuated undesirable side effects. Moieties capable of mediating such effects are disclosed, for example, in *Remington's Pharmaceutical Sciences*, 16th ed., Mack Publishing Co., Easton, Pa. (1980).

Modifications are not limited to the side chains of the amino acids. One may also modify the peptidyl linkage itself, e.g., —NRCO— (where R is alkyl or aryl), instead of —NHCO—, as in the so-called "peptoids."

The peptides may also comprise isoteres of two or more residues in the immunogenic peptide. An isotere as defined here is a sequence of two or more residues that can be sustituted for a second sequence because the steric conformation of the first sequence fits a binding site specific for the second sequence. The term specifically includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, *Chemistry and Biochemistry of Amino Acids, Peptides and Proteins*, Vol. VII (Weinstein ed., 1983).

It is also possible to construct and use so-called peptide mimetics whose conformation is similar to that of a peptide but do not have a peptide-like molecular formula. In effect, in a mimetic, all of the residues of the peptide are replaced by one or more isoteres as defined above.

The Disease-Specific Immunogen

The disease-specific immunogen of the present invention is a molecule corresponding to or otherwise comprising a disease-specific CTL epitope as previously described. The immunogen may comprise one or more disease-specific CTL epitopes, which may be the same or different. Preferably, the immunogen is chosen so that at least one epitope is effective in each of two or more restriction systems, e.g., HLA-A2 and HLA-A3. In some instances, a single epitope may be effective in more than one restriction system. For example HLA-A2 and HLA-69, or HLA-A3 and HLA-A11, are pairs of MHC molecules having similar peptide binding motifs. Otherwise, for the immunogen to be effective in more than one restriction system, two or more epitopes (at least one for each MHC molecule of interest) will need to be provided. These epitopes may be separate or overlapping.

It should be noted that instead of linking epitopes within a single immunogen, the compositions of the present invention may include two or more immunogens which present different epitopes.

If the immunogen comprises a plurality of such epitopes, they may be linked directly, or through a spacer of some kind, or by noncovalent means such as an avidin:biotin complex. The immunogen may take any form that is capable of eliciting a suitable cytotoxic immune response. By way of example and not of limitation, the immunogen may be a fusion of a plurality of CTL epitopes which is sufficiently large to be immunogenic, a conjugate of one or more epitopes to a soluble immunogenic macromolecular carrier, such as serum albumin, keyhole limpet hemocyanin, or dextran, a recombinant virus engineered to display the epitope on its surface, or a conjugate of a plurality of epitopes to a branched lysine core structure, a so-called "multiple antigenic peptide" (see Posnett, et al., J. Biol. Chem., 263:1719–25, 1988).

The immunogenic conjugate may also comprise moieties intended to enhance the immune response, such as a T helper peptide, a cytokine or an adjuvant; a targeting agent, such as an antibody or receptor ligand or ligand analogue; or a stabilizing agent, such as a lipid.

For instance, the ability of the peptides to induce CTL activity can be enhanced by linkage to a sequence which contains at least one epitope that is capable of inducing a T helper cell response. Particularly preferred immunogenic peptides/T helper conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues. Alternatively, the CTL peptide may be linked to the T helper peptide without a spacer.

The immunogenic peptide may be linked to the T helper peptide either directly or via a spacer either at the amino or carboxy terminus of the CTL peptide. The amino terminus of either the immunogenic peptide or the T helper peptide may be acylated.

Melanoma-specific CTL epitopes are of particular interest. Besides one or more of the novel melanoma-specific CTL epitopes described herein, the immunogen may present one or more such epitopes already known in the art, such as the following:

TABLE A

Peptide epitopes for human tumor-specific CTL

| Protein | MHC restriction | Peptide sequence | SEQ ID NO: | Tumor type |
| --- | --- | --- | --- | --- |
| Tyrosinase | A2 | MLLAYLYCL | 66 | Melanoma |
| Tyrosinase | A24 | AFLPWHRLF, | residues 206–214 | Melanoma |
|  |  | AFLPWHRLFL | residues 206–215 |  |
| Tyrosinase | B44 | SEIWRDIDF | residues 192–200 | Melanoma |
| gp 100/Pme117 | A2 | KTWGQYWQV | 82 | Melanoma |
| gp 100/Pme117 | A2 | ITDQVPFSV | 83 | Melanoma |

TABLE A-continued

Peptide epitopes for human tumor-specific CTL

| Protein | MHC restriction | Peptide sequence | SEQ ID NO: | Tumor type |
|---|---|---|---|---|
| gp 100/Pme117 | A2 | VLYRYGSFSV | 84 | Melanoma |
| gp 100/Pme117 | A2 | LLDGTATLRL | 85 | Melanoma |
| MART-1/MelanA | A2 | AAGIGILTV | 86 | Melanoma |
| MART-1/MelanA | A2 | ILTVILGVL | 87 | Melanoma |
| gp 75/TRP-1 | A31 | — | | Melanoma |
| MAGE-1 | A1 | EADPTGHSY | 88 | Melanoma, other tumors[1] |
| MAGE-1 | Cw*1601 | SAYGEPRKL | 89 | Melanoma, other tumors[1] |
| MAGE-3 | A1 | EVDPIGHLY | 90 | Melanoma, other tumors[2] |
| MAGE-3 | A2 | FLWGPRALV | 91 | Melanoma, other tumors[2] |
| BAGE | Cw*1601 | AARAVFLAL | 92 | Melanoma, other tumors[3] |
| GAGE-1,2 | Cw6 | YRPRPRRY | 93 | Melanoma, other tumors[4] |
| HER-2/neu | A2 | KIFGSLAFL, | 94 | Ovarian Cancer |
| | | VMAGVGSPYV | 95 | |
| HER-2/neu | A2 | IISAVVGIL | 96 | Ovarian Cancer, NSCLC |
| CEA | A2 | YLSGANLNL | 97 | Colon Cancer |
| p15 | A24 | (E) AYGLDFYIL | 98 | Melanoma and normal tissues |
| 43 kD protein | A2 | QDLTMKYQIF | 99 | Melanoma |
| MUM-1 gene product mutated across intron/exon junction | B*4402 | EEKLIVVLF[5] | 100 | Melanoma |
| mutated beta-catenin | A24 | SYLDSGIHF[6] | 101 | Melanoma |

[1]MAGE-1: expressed in Melanoma (36%), Bladder CA (19%), Breast CA (18%), Head & neck CA (25%), Non-small cell lung CA (NSCLC, 34%), Sarcomas (11%), Prostate CA (15%) [50]
[2]MAGE-3: expressed in Melanoma (65%), Bladder CA (34%), Breast CA (11%), Head & neck CA (48%), Non-small cell lung CA (NSCLC, 31%), Sarcomas (11%), Prostate CA (15%) [50]
[3]BAGE: expressed in Malanoma (22%), Bladder CA (15%), Breast CA (10%), Head and neck CA (<10%), NSCLC (<10%) [50]
[4]GAGE-1, -2: expressed in Melanoma (24%), Bladder CA (12%), Breast CA (9%), Head & neck CA (19%), NSCLC (19%), Sarcomas (25%), Prostate cancers (10%) [50]
[5]Isoleucine (I) at position 5 is the result of mutation. The wild type sequence is EEKLSVVLF (SEQ ID NO:102)
[6]Phenylalanine (F) at pos. 9 is the result of mutation. The wild type sequence is SYLDSGIHS (SEQ ID NO:103)
Note that the first entry on this table is a tyrosinase A2 epitope which contains a cysteine, and is therefore a candidate for cysteine depletion.

If it is desirable to present more than one CTL epitope, rather than presenting all of the epitopes on a single immunogen, they may be presented on two or more different immunogens. These may be administered separately, or as part of a mixture, e.g., a mixture of epitopic peptides.

Mode of Production

The peptide portion of the immunogens of the present invention may be produced by any conventional technique, including (a) nonbiological synthesis by sequential coupling of component amino acids, (b) production by recombinant DNA techniques in a suitable host cell, and (c) chemical or enzymatic modification of a sequence made by (a) or (b) above.

Gene Expression. The peptides disclosed herein may be produced, recombinantly, in a suitable host, such as bacteria from the genera Bacillus, Escherichia, Salmonella, Erwinia, and yeasts from the genera Hansenula, Kluyveromyces, Pichia, Rhinosporidium, Saccharomyces, and Schizosaccharomyces, or cultured mammalian cells such as COS-1. The more preferred hosts are microorganisms of the species *Pichia pastoris, Bacillus subtilis, Bacillus brevis, Saccharomyces cerevisiae, Escherichia coli* and *Yarrowia lipolytica*. Any promoter, regulatable or constitutive, which is functional in the host may be used to control gene expression.

These sequences may be constructed in such a manner, including the appropriate expression systems for use in gene therapy procedures. Because several different nucleotide sequences may encode a single amino acid, alternate DNA sequences may also encode these peptides.

Standard reference works setting forth the general principles of recombinant DNA technology include Watson, J. D., et al., *Molecular Biology of the Gene*, Volumes I and II, The Benjamin/Cummings Publishing Company, Inc., publisher, Menlo Park, Calif. (1987); Darnell, J. E., et al., *Molecular Cell Biology*, Scientific American Books, Inc., publisher, New York, N.Y. (1986); Lewin, B. M., *Genes II*, John Wiley & Sons, publishers, New York, N.Y. (1985); Old, R. W., et al., *Principles of Gene Manipulation: An Introduction to Genetic Engineering*, 2d edition, University of California Press, publisher, Berkeley, Calif. (1981); Sambrook, J., et al., *Molecular Cloning: A Laboratory Manual*, Cold Spring Harbor Laboratory, Cold Spring Harbor, N.Y. (1989); and Ausubel, et al., *Current Protocols in Molecular Biology*, Wiley Interscience, N.Y., (1987, 1992). These references are herein entirely incorporated by reference.

Chemical Peptide Synthesis. Chemical peptide synthesis is a rapidly evolving area in the art, and methods of solid phase peptide synthesis are well-described in the following references, hereby entirely incorporated by reference: (Merrifield, B., *J. Amer. Chem. Soc.* 85:2149–2154 (1963); Merrifield, B., *Science* 232:341–347 (1986); Wade, J. D., et al., *Biopolymers* 25:S21–S37 (1986); Fields, G. B., *Int. J. Polypeptide Prot. Res.* 35:161 (1990); MilliGen Report Nos. 2 and 2a, Millipore Corporation, Bedford, Mass., 1987) Ausubel, et al, supra, and Sambrook, et al, supra.

In general, as is known in the art, such methods involve blocking or protecting reactive functional groups, such as free amino, carboxyl and thio groups. After polypeptide bond formation, the protective groups are removed (or de-protected). Thus, the addition of each amino acid residue requires several reaction steps for protecting and deprotecting. Current methods utilize solid phase synthesis, wherein the C-terminal amino acid is covalently linked to an insoluble resin particle large enough to be separated from the fluid phase by filtration. Thus, reactants are removed by washing the resin particles with appropriate solvents using an automated programmed machine. The completed polypeptide chain is cleaved from the resin by a reaction which does not affect polypeptide bonds.

In the more classical method, known as the "tBoc method," the amino group of the amino acid being added to the resin-bound C-terminal amino acid is blocked with tert-butyloxycarbonyl chloride (tBoc). This protected amino acid is reacted with the bound amino acid in the presence of the condensing agent dicyclohexylcarbodiimide, allowing its carboxyl group to form a polypeptide bond the free amino group of the bound amino acid. The amino-blocking group is then removed by acidification with trifluoroacetic acid (TFA); it subsequently decomposes into gaseous carbon dioxide and isobutylene. These steps are repeated cyclically for each additional amino acid residue. A more vigorous treatment with hydrogen fluoride (HF) or trifluoromethane-sulfonyl derivatives is common at the end of the synthesis to cleave the benzyl-derived side chain protecting groups and the polypeptide-resin bond.

More recently, the preferred "Fmoc" technique has been introduced as an alternative synthetic approach, offering milder reaction conditions, simpler activation procedures and compatibility with continuous flow techniques. This method was used, e.g., to prepare the peptide sequences disclosed in the present application. Here, the -amino group is protected by the base labile 9-fluorenylmethoxycarbonyl (Fmoc) group. The benzyl side chain protecting groups are replaced by the more acid labile t-butyl derivatives. Repetitive acid treatments are replaced by deprotection with mild base solutions, e.g., 20% piperidine in dimethylformamide (DMF), and the final HF cleavage treatment is eliminated. A TFA solution is used instead to cleave side chain protecting groups and the peptide resin linkage simultaneously.

At least three different peptide-resin linkage agents can be used: substituted benzyl alcohol derivatives that can be cleaved with 95% TFA to produce a peptide acid, methanolic ammonia to produce a peptide amide, or 1% TFA to produce a protected peptide which can then be used in fragment condensation procedures, as described by Atherton, E., et al., *J. Chem. Soc. Perkin Trans.* 1:538–546 (1981) and Sheppard, R. C., et al., *Int. J. Polypeptide Prot. Res.* 20:451–454 (1982). Furthermore, highly reactive Fmoc amino acids are available as pentafluorophenyl esters or dihydro-oxobenzotriazine esters derivatives, saving the step of activation used in the tBoc method.

Pharmaceutical Methods and Preparations

The preferred animal subject of the present invention is a primate mammal. By the term "mammal" is meant an individual belonging to the class Mammalia, which, of course, includes humans. The invention is particularly useful in the treatment of human subjects, although it is intended for veterinary uses as well. By the term "non-human primate" is intended any member of the suborder Anthropoidea except for the family Hominidae. Such non-human primates include the superfamily Ceboidea, family Cebidae (the New World monkeys including the capuchins, howlers, spider monkeys and squirrel monkeys) and family Callithricidae (including the marmosets); the superfamily Cercopithecoidea, family Cercopithecidae (including the macaques, mandrills, baboons, proboscis monkeys, mona monkeys, and the sacred hunaman monkeys of India); and superfamily Hominoidea, family Pongidae (including gibbons, orangutans, gorillas, and chimpanzees). The rhesus monkey is one member of the macaques.

The term "protection", as used herein, is intended to include "prevention," "suppression" and "treatment." "Prevention" involves administration of the protein prior to the induction of the disease. "Suppression" involves administration of the composition Prior to the clinical appearance of the disease. "Treatment" involves administration of the protective composition after the appearance of the disease.

It will be understood that in human and veterinary medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis." It should also be understood that to be useful, the protection provided need not be absolute, provided that it is sufficient to carry clinical value. An agent which provides protection to a lesser degree than do competitive agents may still be of value if the other agents are ineffective for a particular individual, if it can be used in combination with other agents to enhance the level of protection, or if it is safer than competitive agents.

The composition may be administered parentally or orally, and, if parentally, either systemically or topically. Parenteral routes include subcutaneous, intravenous intradermal, intramuscular, intraperitoneal, intranasal, transdermal, or buccal routes. One or more such routes may be employed. Parenteral administration can be, e.g., by bolus injection or by gradual perfusion over time. Alternatively, or concurrently, administration may be by the oral route. The immunization is preferably accomplished initially by intramuscular injection followed by intradermal injection, although any combination of intradermal and intramuscular injections may be used.

It is understood that the suitable dosage of a immunogen of the present invention will be dependent upon the age, sex, health, and weight of the recipient, kind of concurrent treatment, if any, frequency of treatment, and the nature of the effect desired. However, the most preferred dosage can be tailored to the individual subject, as is understood and determinable by one of skill in the art, without undue experimentation. This will typically involve adjustment of a standard dose, e.g., reduction of the dose if the patient has a low body weight.

Prior to use in humans, a drug will first be evaluated for safety and efficacy in laboratory animals. In human clinical studies, one would begin with a dose expected to be safe in humans, based on the preclinical data for the drug in question, and on customary doses for analogous drugs (if any). If this dose is effective, the dosage may be decreased, to determine the minimum effective dose, if desired. If this dose is ineffective, it will be cautiously increased, with the patients monitored for signs of side effects. See, e.g., Berkow, et al., eds., *The Merck Manual*, 15th edition, Merck and Co., Rahway, N.J., 1987; Goodman, et al., eds., *Goodman and Gilman's The Pharmacological Basis of Therapeutics*, 8th edition, Pergamon Press, Inc., Elmsford, N.Y., (1990); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston, (1985), which references and references cited therein, are entirely incorporated herein by reference.

The total dose required for each treatment may be administered in multiple doses (which may be the same or different) or in a single dose, according to an immunization schedule, which may be predetermined or ad hoc. The schedule is selected so as to be immunologically effective, i.e., so as to be sufficient to elicit an effective CTL response to the antigen and thereby, possibly in conjunction with other agents, to provide protection. The doses adequate to accomplish this are defined as "therapeutically effective doses." (Note that a schedule may be immunologically effective even though an individual dose, if administered by itself, would not be effective, and the meaning of "therapeutically effective dose" is best interpreted in the context of the immunization schedule.) Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 $\mu$g to about 5000 $\mu$g of peptide for a 70 kg patient, followed by boosting dosages of from about 1.0 $\mu$g to about 1000 $\mu$g of peptide pursuant to a boosting regimen over weeks to months depending upon the patient's response and condition by measuring specific CTL activity in the patient's blood. It must be kept in mind that the peptides and compositions of the present invention may generally be employed in serious disease states, that is, life-threatening or potentially life threatening situations. In such cases, in view of the inimization of extraneous substances and the relative nontoxic nature of the peptides, it is possible and may be felt desirable by the treating physician to administer substantial excesses of these peptide compositions.

The doses may be given at any intervals which are effective. If the interval is too short, immunoparalysis or other adverse effects can occur. If the interval is too long, immunity may suffer. The optimum interval may be longer if the individual doses are larger. Typical intervals are 1 week, 2 weeks, 4 weeks (or one month), 6 weeks, 8 weeks (or two months) and one year. The appropriateness of administering additional doses, and of increasing or decreasing the interval, may be reevaluated on a continuing basis, in view of the patient's immunocompetence (e.g., the level of antibodies to melanoma-associated antigens).

The concentration of CTL stimulatory peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

In one embodiment, the immunogen is dissolved or suspended in an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The peptides of the invention may also be administered via liposomes, which serve to target the peptides to a particular tissue, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among melanocytes or melanomas, or with other therapeutic or immunogenic compositions. Thus, liposomes filled with a desired peptide of the invention can be directed to the site of target cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019,369, incorporated herein by reference.

For targeting to the melanoma cells, a ligand to be incorporated into the liposome can include, e.g., antibodies or fragments thereof specific for cell surface determinants of the desired melanoma cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, the immunogenic peptides are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. the balance of the composition is ordinarily propellant. A carrier can also be included, as desired, as with, e.g., lecithin for intranasal delivery.

In addition to the peptides or analogues of the invention, a pharmaceutical composition may contain suitable pharmaceutically acceptable carriers, such as excipients, carriers and/or auxiliaries which facilitate processing of the active compounds into preparations which can be used pharmaceutically.

The appropriate dosage form will depend on the disease, the immunogen, and the mode of administration; possibilities include tablets, capsules, lozenges, dental pastes, suppositories, inhalants, solutions, ointments and parenteral depots. See, e.g., Berker, supra, Goodman, supra, Avery, supra and Ebadi, supra, which are entirely incorporated herein by reference, including all references cited therein. However, it is expected that each vaccine preparation will include 1–100 $\mu$g of the peptide epitope.

The composition may also include an adjuvant. Typical adjuvants include proteins, peptides, carbohydrates, lipids and liposaccharides. An example of a currently popular adjuvant is DETOX (Ribi Immunochemicals)(muramyl dipeptide and cell wall fragments from *Mycobacterium phlei*). Other adjuvants include QS-21, Montanide ISA-21, incomplete Freund's adjuvant, aluminum phosphate, aluminum hydroxide, alum, DEAE-dextran, saponin, and mineral oil. Montanide ISA-51 is manufactured by Seppic, Inc. (75 Quai D'Orsay, 75321, Paris, France). Its composition is manide oleate in mineral oil solution.

QS-21 is manufactured by Cambridge Biotech (365 Plantation Street, Worcester, Mass. 01605-2376). It is a triterpene glycoside isolated from the bark of a South American tree (*Quillaja saponaria*). The tradename for QS-21 is Stimulon™. Its molecular formula is $C_{92}O_{46}H_{148}$, and its molecular weight is 1,990. Its complete chemical name is 3-O-β-D-galactopyranosyl-(1→2)-[β-D-xylopyranosyl-(1→3)]-β-D-glucuronpyranosyl-quillaic acid 28-O-β-D-apiofuranosyl-(1→3)-β-D-xylopyranosyl-(1→4)-α-L-rhamnopyranosyl-(1→2)-3-[5-O-α-L-arabinofuranosyl 3,5-dihydroxy-6-methyloctanoyl]-3,5-dihydroxy-6-methyloctanoyl]-β-D-fucopyranoside.

If desired, the adjuvant may be conjugated to the epitope and not simply a part of a mixture. See Deres, et al, Nature, 342:561–4 (1989).

The composition may also include an immunomodulator, especially cytokines such as IL-1, IL-2, IL-4, IL-6, IL-7, IL-12, Interferon-alpha, Interferon-gamma, Granulocyte Macrophage Colony Stimulating Factor (GMCSF), Tumor Necrosis Factor (TNF)-alpha, and TNF-beta.

The composition may also include antigen-presenting cells, such as dendritic cells or macrophages. Preferably, the APCs are harvested, e.g., from peripheral blood or bone marrow, conjugated, covalently or noncovalently (e.g., by pulsing) to the immunogen, e.g., a peptide, and administered to the patient.

The composition may also include a molecule which activates or helps in activating CTLs, such as a CD-28 stimulatory molecule (e.g., B7.1, B7.2, or anti-CD28). If the molecule may be administered in place of the molecule itself.

CD80 (B7 BB1) is expressed on activated B cells and dendritic cells. It is a ligand for CD28 and CTLA-4. It has been found to represent two (partially homologous) proteins, B7-1 and B7-2. See Ramarathinam, et al. T cell costimulation by B7/BB1 induces CD8 T-cell-dependent tumor rejection: an important role of B7/BB1 in the induction, recruitment, and effector function of antitumor T cells. J. Exp. Med. 1994: 1790: 1205–1214; Freeman et al. Cloning of B7-2: a CTLA-4 counter-receptor that costimulates human T cell proliferation. Science 1993, 262: 909–911; Li et al. Costimulation of tumor-reactive CD4+ and CD8+ T lymphocytes by B7, a natural ligand for CD28, can be used to treat established mouse melanoma. J. Immunol. 1994, 153: 421–428; Hodge et al. Admixture of a recombinant vaccinia virus containing the gene for the costimulator molecule B7 and a recombinant vaccinia virus containing a tumor-associated antigen gene results in enhanced specific T-cell responses antitumor immunity. Cancer Res. 1995, 55: 3598–3603.

A pharmaceutical composition according to the present invention may further comprise at least one cancer chemotherapeutic compound, such as one selected from the group consisting of an anti-metabolite, a bleomycin peptide antibiotic, a podophyllin alkaloid, a Vinca alkaloid, an alkylating agent, an antibiotic, cisplatin, or a nitrosourea. A pharmaceutical composition according to the present invention may further or additionally comprise at least one viral chemotherapeutic compound selected from gamma globulin, amantadine, guanidine, hydroxybenzimidazole, interferon-α, interferon-β, interferon-γ, thiosemicarbarzones, methisazone, rifampin, ribvirin, a pyrimidine analog, a purine analog, foscarnet, phosphonoacetic acid, acyclovir, dideoxynucleosides, or ganciclovir. See, e.g., Katzung, supra, and the references cited therein on pages 798–800 and 680–681, respectively, which references are herein entirely incorporated by reference.

As an alternative to a pharmaceutical composition comprising the immunogen of the present invention, per se, the pharmaceutical composition may instead comprise a vector comprising an expressible gene encoding such an immunogen. The pharmaceutical composition and method would then be chosen so that the vector was delivered to suitable cells of the subject, so that the gene would be expressed and the immunogen produced in such a manner as to elicit an immune response. A preferred vector would be a Vaccinia virus, such as a construct containing a minigene encoding the peptide of interest. In the case of genes encoding naturally occurring proteins, or peptide fragments thereof, one may, but need not, use the DNA sequence which encodes the proteins or peptides in nature. A preferred route for immunization would be scarification. A preferred immunization protocol would be 10E6 to 10E8 pfu/dose in the initial injection, followed up with boosters at 1,3 and 12 months. The boosters could be the previously described immunogen-containing composition.

In the case of genes encoding naturally occurring proteins, or peptide fragments thereof, one may, but need not, use the DNA sequence which encodes the proteins or peptides in nature.

Recombinant vaccinia virus constructs have been used for immunization against hepatitis B (Moss, et al., *Nature*, 311, 67, 1984), herpes simplex virus (Wacchsman, et al., *Biosci. Rep.* 8, 323; 334, 1988), parainfluenza type 3 (Spriggs, et al., *J. Virol.*, 62, 1293, 1988), and Lassa fever virus (Fisher-Hoch, et al., *Proc. Natl. Acad. Sci. USA*, 86, 317, 1989). Vaccinia virus constructs comprising gene for cancer-associated antigens have also been prepared (Lathe, et al., *Nature*, 326, 878, 1987; Bernards, et al., *Proc. Natl. Acad. Sci. USA*, 84, 6854, 1987; Estin, et al., *Proc. Natl. Acad. Sci. USA*, 85, 1052, 1988).

Alternatively or additionally, the composition may comprise disease-specific CTL. Antigenic peptides may be used to elicit CTL ex vivo. Ex vivo CTL responses to an antigen are induced by incubating in tissue culture the patient's CTL precursor cells (CTLp) together with a source of antigen-presenting cells (APC) and the appropriate immunogenic peptide. After an appropriate incubation time (typically 1–8 weeks), in which the CTLp are activated and mature and expand into effector CTL, the cells are infused back into the patient, where they will destroy their specific target cell. In order to optimize the in vitro conditions for the generation of specific cytotoxic T cells, the culture of stimulator cells may be maintained in an appropriate serum-free medium.

Prior to incubation of the stimulator cells with the cells to be activated, e.g., precursor CD8+ cells, an amount of antigenic peptide is added to the stimulator cell culture, of sufficient quantity to become loaded onto the human Class I molecules to be expressed on the surface of the stimulator cells. In the present invention, a sufficient amount of peptide is an amount that will allow about 200, and preferably 200 or more, human Class I MHC molecules loaded with peptide to be expressed on the surface of each stimulator cell.

Preferably, the stimulator cells are incubated with at least 1 mg/ml, more preferably >20 µg/ml peptide.

Resting or precursor CD8+ cells are then incubated in culture with the appropriate stimulator cells for a time period sufficient to activate the CD8+ cells. Preferably, the CD8+ cells are activated in an antigen-specific manner. The ratio of resting or precursor CD8+ (effector) cells to stimulator cells may vary from individual to individual and may further depend upon variables such as the amenability of an individual's lymphocytes to culturing conditions and the nature and severity of the disease condition or other condition for which the within-described treatment modality is used. Preferably, however, the lymphocyte:stimulator cell ratio is in the range of about 1:5 to 20:1, more preferably 3:1 to 5:1. The effector/stimulator culture may be maintained for as long a time as is necessary to stimulate a therapeutically useful or effective number of CD8+ cells.

The induction of CTL in vitro requires the specific recognition of peptides that are bound to allele specific MHC class I molecules on APC. The number of specific MHC/peptide complexes per APC is crucial for the stimulation of CTL, particularly in primary immune responses. While small amounts of peptide/MHC complexes per cell are sufficient to render a cell susceptible to lysis by CTL, or to stimulate a secondary CTL response, the successful activation of a CTL precursor (pCTL) during primary response requires a significantly higher number of MHC/peptide complexes. Peptide loading of empty major histocompatability complex molecules on cells allows the induction of primary cytotoxic T lymphocyte responses.

Often it is useful, in the generation of peptide-specific CTL, to stimulate with mutant cell lines that have some empty MHC molecules. An exmample is the human lymphoid cell line, T2. However, mutant cell lines expressing every MHC molecule are not yet available. Thus, in some cases, it may be useful to strip endogenous MHC-associated peptides from the surface of APC, followed by loading the resulting empty MHC molecules with the immunogenic peptides of interest. The use of non-transformed (non-tumorigenic), non-infected cells, and preferably, autologous cells of patients as APC is desirable for the design of CTL induction protocols directed towards development of ex vivo CTL therapies. This application discloses methods for stripping the endogenous MHC-associated peptides from the surface of APC followed by the loading of desired peptides.

A stable MHC class I molecule is a trimeric complex formed of the following elements: 1) a peptide usually of 8–10 residues, 2) a transmembrane heavy polymorphic protein chain which bears the peptide-binding site in its α1 and α2 domains, and 3) a non-covalently associated non-polymorphic light chain, $\beta_2$microglobulin. Removing the bound peptides and/or dissociating the $\beta_2$microglobulin from the complex renders the MHC class I molecules nonfunctional and unstable, resulting in rapid degradation. All MHC class I molecules isolated from PBMCs have endogenous peptides bound to them. Therefore, the first step is to remove all endogenous peptides bound to MHC class I molecules on the APC without causing their degradation before exogenous peptides can be added to them.

Two possible ways to free up MHC class I molecules of bound peptides include the culture temperature from 37° C. to 26° C. overnight to destabilize $\beta_2$microglobulin and stripping the endogenous peptides from the cell using a mild acid treatment. The methods release previously bound peptides into the extracellular environment allowing new exogenous peptides to bind to the empty class I molecules. The cold-temperature incubation method enables exogenous peptides to bind efficiently to the MHC complex, but requires an overnight incubation at 26° C. which may slow the cell's metabolic rate. It is also likely that cells not actively synthesizing MHC molecules (e.g., resting PBMC) would not produce high amounts of empty surface MHC molecules by the cold temperature procedure.

Harsh acid stripping involves extraction of the peptides with trifluoroacetic acid, pH 2, or acid denaturation of the immunoaffinity purified class I-peptide complexes. These methods are not feasible for CTL induction, since it is important to remove the endogenous peptides while preserving APC viability and an optimal metabolic state which is critical for antigen presentation. Mild acid solutions of pH 3 such as glycine or citrate-phosphate buffers have been used to identify endogenous peptides and to identify tumor associated T cell epitopes. The treatment is especially effective, in that only the MHC class I molecules are destabilized (and associated peptides released), while other surface antigens remain intact, including MHC class II molecules. Most importantly, treatment of cells with the mild acid solutions do not affect the cell's viability or metabolic state. The mild acid treatment is rapid since the stripping of the endogenous peptides occurs in two minutes at 4° C. and the APC is ready to perform its function after the appropriate peptides are loaded. The technique is utilized herein to make peptide-specific APCs for the generation of primary antigen-specific CTL. The resulting APC are efficient in inducing peptide-specific CD8+ CTL.

Activated CD8+ cells may be effectively separated from the stimulator cells using one of a variety of known methods. For example, monoclonal antibodies specific for the stimulator cells, for the peptides loaded onto the stimulator cells, or for the CD8+ cells (or a segment thereof) may be utilized to bind their appropriate complementary ligand. Antibody-tagged molecules may then be extracted from the stimulator-effector cell admixture via appropriate means, e.g., via well-known immunoprecipitation or immunoassay methods.

Effective, cytotoxic amounts of the activated CD8+ cells can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1\times10^6$ to about $1\times10^{12}$, more preferably about $1\times10^8$ to about $1\times10^{11}$, and even more preferably, about $1\times10^9$ to about $1\times10^{10}$ activated CD8+ cells are utilized for adult humans, compared to about $5\times10^6$–$5\times10^7$ cells are used in mice.

Preferably, as discussed above, the activated CD8+ cells are harvested from the cell culture prior to administration of the CD8+ cells to the individual being treated. It is important to note, however, that unlike other present and proposed treatment modalities, the present method preferably uses a cell culture system that is not tumorigenic. Therefore, if complete separation of stimulator cells and activated CD8+ cells is not achieved, there is no inherent danger known to be associated with the administration of a small number of stimulator cells, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8+ cells via intravenous infusion is appropriate.

Adoptive transfer of melanoma-specific CTL has been accompanied by tumor shrinkage in a large minority of patients with advanced melanoma and by disappearance of all detectable tumor in a smaller proportion of patients. (Rosenberg et al, NEM 319: 1676–1680, 1988) and in animal studies appears to be particularly promising for the treatment of solid tumors (Rosenberg SA et al. Science 233:1318–1321). One of the problems with existing methods for CTL generation is that they require the resection of large metastic tumor deposits to initiate the process. If the requirement for available autologous tumor could be circumvented, then patients with no measurable disease but a high risk of recurrence (eg, melanoma patients with primary tumors greater than 4 mm thick or with microscopic tumor metastatic to regional nodes) could be treated with adoptive therapy even if their tumor were removed and fixed in formalin and no other gross tumor was evident. These patients have a very high likelihood of harboring micrometastic disease for which no other effective therapy is now available; so most will die of the melanoma. It is possible that the presence of bulky tumor suppresses the autologous immune response; so treatment of patients without bulky disease would be an attractive goal. Especially in murine systems, CTL have been generated and maintained by stimulation with cells to which the peptide epitope has been bound. We propose that, e.g., HLA-A2.1+ or HLA-A3+ cells (autologous B cells, macrophages, or dendritic cells, ideally), would be pulsed in vitro with peptide (e.g., a cysteine-depleted form of peptide KCDICTDEY (SEQ ID NO:19)) and used as in vitro simulators for autologous lymph node cells or peripheral blood lymphocytes. The patients could be pre-stimulated with a peptide vaccine prior to lymphocyte harvest if the existing response was inadequate. Lymphocytes stimulated with peptide in vitro could then be expanded to $10^{10}$ or $10^{11}$ cells, then re-infused into the patients in a manner analogous to that used for LAK cell therapy. It is expected that the adoptively transferred CTL would survive best with IL-2 infusion at low to intermediate doses, and that putative inhibitors of Tc suppression (eg: cyclophosphamide) may be employed also, prior to the infusions of CTL.

Clinical studies with adoptive immunotherapy using A2-restricted tumor infiltrating lymphocytes (TIL) have shown a strong correlation between Pmel-17/gp100 reactivity and positive clinical responses of patients treated with those TIL. Kawakami, et al., J. Immunol., 154:3961–8 (1995).

Disease-Specific Diagnostic Agents

A melanoma-specific diagnostic agent is (1) a molecule which is or which comprises a disease-specific epitope as previously defined, and which is labeled, immobilized, or otherwise rendered suitable for diagnostic use, or (2) an antibody which specifically binds such a disease-specific epitope, and which is labeled, immobilized, or otherwise rendered suitable for diagnostic use, or (3) a T-cell line (e.g., murine or human), which specifically recognizes a disease-specific epitope.

Diagnostic Uses and Compositions

The relationship between the host's immune response and his or her tumor is poorly understood. Better understanding of that response depends on evaluation of the specific responses against individual epitopes. If patients do have an immune response to an epitope naturally, then evaluation and quantitation of that by precursor frequency analysis of the CTL in the patient's blood pool may permit some assessment of the protection that person's immune system is providing. As new therapies become available for melanoma, it may be useful to screen patients for the presence of the peptide on their tumor and the presence of CTL in their blood pool with specificity for the peptide on appropriate cells. These findings may determine whether further augmentation of the immune response is indicated or whether other, non-immunologic, therapy should be employed. A parallel to this is the determination on breast cancers of the presence of estrogen and progesterone receptors before considering hormonal therapy or chemotherapy.

Thus, the peptides of the present invention may be used to screen a sample for the presence of an antigen with the same epitope, or with a different but cross-reactive epitope, or for the presence of CTLs which specifically recognize the corresponding epitopes. The sample will normally be a biological fluid, such as blood, urine, lymphatic fluid, amniotic fluid, semen, saliva, tears, milk, or cerebrospinal fluid, or a fraction or derivative thereof, or a biological tissue, in the form of, e.g., a tissue section or homogenate. The preferred sample is blood, or a fraction or derivative thereof.

Assays may be divided into two basic types, heterogeneous and homogeneous. In heterogeneous assays, the interaction between the affinity molecule and the analyte does not affect the label, hence, to determine the amount or presence of analyte, bound label must be separated from free label. In homogeneous assays, the interaction does affect the activity of the label, and therefore analyte levels can be deduced without the need for a separation step.

Assays may also be divided into competitive and non-competitive formats. In the competitive format, the analyte competes with a labeled analyte analogue for binding to a binding partner. In a common noncompetitive format called a sandwich assay, the analyte is first bound by a capture reagent, and then by a tag reagent.

In order to detect the presence, or measure the amount, of an analyte, the assay must provide for a signal producing system (SPS) in which there is a detectable difference in the signal produced, depending on whether the analyte is present or absent (or, in a quantitative assay, on the amount of the analyte). The detectable signal may be one which is visually detectable, or one detectable only with instruments. Possible signals include production of colored or luminescent products, alteration of the characteristics (including amplitude or polarization) of absorption or emission of radiation by an assay component or product, and precipitation or agglutination of a component or product. The term "signal" is intended to include the discontinuance of an existing signal, or a change in the rate of change of an observable parameter, rather than a change in its absolute value. The signal may be monitored manually or automatically.

The component of the signal producing system which is most intimately associated with the diagnostic reagent is called the "label". A label may be, e.g., a radioisotope, a fluorophore, an enzyme, a co-enzyme, an enzyme substrate, an electron-dense compound, an agglutinable particle.

The radioactive isotope can be detected by such means as the use of a gamma counter or a scintillation counter or by autoradiography. Isotopes which are particularly useful for the purpose of the present invention are $^{3}H$, $^{125}I$, $^{131}I$, $^{35}S$, $^{14}C$, and, preferably, $^{125}I$.

It is also possible to label a compound with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

Alternatively, fluorescence-emitting metals such as $^{125}Eu$, or others of the lanthanide series, may be attached to the binding protein using such metal chelating groups as diethyl-enetriaminepentaacetic acid (DTPA) and ethylenediamine-tetraacetic acid (EDTA).

The peptides also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are luminol, isolumino, theromatic acridinium ester, imidazole, acridinium salt and oxalate ester.

Likewise, a bioluminescent compound may be used to label the peptides. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Enzyme labels, such as horseradish peroxidase, alkaline phosphatase, malate dehydrogenase, staphylococcal nuclease, δ-V-steroid isomerase, yeast alcohol dehydrogenase, α-glycero phosphate dehydrogenase, triose phosphate isomerase, asparaginase, glucose oxidase, β-galactosidase, ribonuclease, glucose-6-phosphate dehydrogenase, glucoamylase and acetylcholine esterase, are preferred. When an enzyme label is used, the signal producing system must also include a substrate for the enzyme. If the enzymatic reaction product is not itself detectable, the SPS will include one or more additional reactants so that a detectable product appears.

A label may be conjugated, directly or indirectly (e.g., through a labeled antibody), covalently (e.g., with SPDP) or noncovalently, to the peptide, to produce a diagnostic reagent. Similarly, the peptide may be conjugated to a solid phase support to form a solid phase ("capture") diagnostic reagent. Suitable supports include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to its target. Thus the support configuration may be spherical, as in a bead, or cylindrical, as in the inside surface of a test tube, or the external surface of a rod. Alternatively, the surface may be flat such as a sheet, test strip, etc.

Additionally, the peptides may be used as a diagnostic tool to evaluate whether other immunotherapeutic treatments (tumor vaccines of any kind, adoptive transfer of CTL, etc) are having a beneficial effect.

Generation of Tumor-specific Cytotoxic T Cells

Detailed methods of CTL generation have been previously reported. Malignant melanoma metastatic to cervical lymph nodes was resected from an 80-yr old patient designated VMM5. The nodes were mechanically dissociated and then enzymatically digested in Eagle's MEM (GIBCO, Grand Island, N.Y.) containing 2.5% FCS (GIBCO, or Whittaker, Walkersville, Md.), 0.1% collagenase B (Boehringer-Mannheim, Indianapolis, Ind.), 0.002% DNase (Sigma, St. Louis, Mo.), penicillin 100 U/ml, streptomycin 100 microg/ml (Pen-Strept, GIBCO) at room temperature. After 4 h, dissociated cells were collected and cryopreserved. Remaining tumor fragments were returned to the digestion media overnight. The digests were harvested in a similar fashion daily for 3 days, with viable tumor cells and lymphocytes obtained each day. These cells were cryopreserved in FCS+10% DMSO in liquid nitrogen. Initial cultures were established with the mixture of lymphocytes and tumor from the tumor-involved node. The ratio of tumor cells to lymphocytes placed in culture were approximately 1:1. The cells were cultured in 24-well tissue culture plates (Linbro, Hamden, Conn.) in RPMI 1640 (Sigma) containing 10% FCS, Pen-Strept, and 20 U/ml rIL-2 (Cetus, Emeryville, Calif.). The CTL were restimulated with irradiated (100 Gy) fresh cryo-preserved autologous tumor (VMM5) at a TLR (tumor:lymphocyte ratio) of 1:10 on day 16. Beginning with the third in vitro stimulation (day 32), and thereafter every 10 to 15 days, the CTL were restimulated with the allogeneic HLA-A2.1$^+$ melanoma cell line DM6. A TLR of 1:5 was used until the cells were 70 days old, after which a TLR between 1:2 and 2:1 was used. Several VMM5 CTL lines were generated following this protocol closely and with consistent results from each. Similar methods were enployed for generation of other CTL lines studied.

Cytotoxicity Assays

Cell-mediated killing was determined in vitro using a 4-h chromium release assay. 51Cr-labeled target cells were plated at $2\times10^3$ cells/well in triplicate on 96-well V-bottom plates (Costar, Cambridge, Mass.) with varying numbers of effector cells in a final volume of 250 microl. Wells containing either culture medium and target cells only or 1 M HCl and target cells served as background 51Cr release controls and total release controls, respectively. The plates were centrifuged at 100×g for 3 min and incubated at 37° C. in 5% CO2 for 4 h. The plates were again centrifuged, and 0.20 ml of medium from each well was removed for counting gamma counter. The cytotoxic index was calculated as:

$$\frac{Cpm \text{ (experimental)} - cpm \text{ (background)}}{Cpm \text{ (total release)} - cpm \text{ (background)}} \times 100\%$$

Lytic units were calculated for several of the cytotoxicity assays, using a software package prepared by the National Cancer Institute (Bethesda, MD), which solves for the equation $y=A\times[1-\exp(-kx)]$, where x is the E:T ratio, y is the cytotoxic index, A is the curve maximum, and k is a constant used to calculate the slope of the best fit line. For the purposes of this study, a lytic unit was defined as the number of effector cells needed to mediate 30% lysis of target cells. The number of lytic units was calculated per $10^5$ effector cells (LU30 per $10^5$ cells).

Prior Examples

The identification of melanoma-specific HLA-A2 and HLA-A3 epitopes is described in WO95/22561 and PCT/US97/04958, both incorporated by reference herein.

EXAMPLE A1-1

Identification of a Tyrosinase Epitope Recognized by Human Melanoma-Reactive, HLA-A1 Restricted CTLs Introduction We have identified the peptide KCDICTDEY (SEQ ID NO:19) (K is N-terminal), from the tyrosinase protein, as an epitope for HLA-A1-restricted melanoma-specific cytotoxic T-lymphocytes (CTL). This work has been done by generating HLA-A1-restricted melanoma-reactive CTL, creating a vaccinia construct encoding the intact human tyrosinase gene, then infecting HLA-A1+ non-melanoma target cells with the vac-tyrosinase construct. In doing so, VMM12 CTL and VMM15 CTL both recognize an HLA-A1-associated peptide derived from tyrosinase. We have since screened a large panel of peptides that we predicted to bind to HLA-A1, from the defined sequence of tyrosinase. The peptide KCDICTDEY (SEQ ID NO:19), when pulsed onto HLA-A1+ non-melanoma cells (C1R-A1), reconstitutes an epitope for VMM15 CTL. To a lesser extent, two other peptides that are longer than 9-residues, but which contain the entire KCDICTDEY (SEQ ID NO:19) sequence, also reconstitute an epitope for these CTL. None of 116 other peptides tested worked. Thus, we believe this is an epitope which can be used as an immunogen in treating or preventing melanoma in the 20–25% of patients who express HLA-A1. Cell lines and HLA typing: The human melanoma cell lines VMM1, VMM12, VMM15, VMM18, VMM30 and VMM34 were derived from patients at the University of Virginia (Charlottesville, Va.). Other fresh (uncultured) tumors VMM14, VMM21 and VMM40 were also prepared from surgical specimens from patients at the University of Virginia. DM6 and DM331 were provided by Drs. H. F. Seigler and T. L. Darrow at Duke University (Durham, N.C.). Immunohistochemical staining of these cell lines with S-100, HMB-45 and vimentin antibodies was characteristic of melanoma, while staining for epithelial membrane antigen and cytokeratin was negative. The Na8Mel and Na8Mel+Tyr cell lines were a gift from Vincent Brichard and Thierry Boon. Na8Mel is a tyrosinase-negative human melanoma line, and Na8Mel+Tyr was derived from transfection of Na8Mel with the tyrosinase cDNA 123. B2. The human melanoma line SkMel24 was obtained from the American Type Culture Collection. The CV-1 and 143B TK- lines used in the propagation of vaccinia virus were also obtained from the American Type Culture Collection (ATCC, Bethesda, Md.). VMM12-Epstein-Barr-virus-(EBV)-transformed B lymphoblastoids cell lines (B-LCL) were generated from peripheral blood mononuclear cells (PBMC) of melanoma patient VMM12. Briefly, the PBMC were incubated with filtered supernatant from the EBV producing cell line B-958 for 1 h at 37° C., followed by culture in RPMI 1640 media with 10% fetal calf serum (FCS) and antibiotics, plus a 1:100 dilution of PHA. K562 is an NK-sensitive human erythroleukemia line. T2-A3 (an HLA-A3 transfectant of the antigen-processing-defective mutant human lymphoid cell line, T2) was provided by P. Cresswell. HLA typing was performed by microcytotoxicity assay on autologous lymphocytes (Gentrak). The HLA class I transfectants of the C1R cell line (C1R-A1, C1R-A3, C1R-B7, and C1R-B8) were kindly provided by Dr. Peter Cresswell (Yale University, New Haven, Conn.). Expression of HLA-A1 and -A3 by tumor cells was confirmed by staining with the monoclonal antibodies HA-A1 (One Lambda, Canoga Park, Calif.) and GAP-A3 (kindly provided by P. Cresswell). Melanoma reactive CTL from peripheral blood lymphocytes, from tumor-involved nodes, or from tumor-draining nodes were generated in vitro by repeated stimulation with autologous tumor cells. Tissue culture media used for the human cell lines was RPMI-1640 (Sigma) supplemented with 10% fetal calf serum, glutamine, and antibiotics, hereafter referred to simply as RPMI.

CTL lines: We have generated human melanoma-specific CTL lines by in vitro stimulation with autologous tumor, from patients whose tumors express melanocytic tissue differentiation antigens and express one or more of the MHC molecules A1, A3, B7, and B8. Methods for CTL generation have been described.

Production of recombinant vaccinia virus expressing the human genes encodina melanocytic tissue differentiation antigens:

We have examined class I MHC-associated epitopes for the melanocytic tissue differentiation antigens by using vaccinia constructs for each of the genes Pmel17/gp100, tyrosinase, and MART-1/MelanA. A cDNA clone of the Pmel17 gene (HUMPMEL17-Genbank) was generously provided by S. N. Wagner, Essen, Germany. The tyrosinase gene was provided by Thierry Boon, Brussels. We have PCR cloned out a cDNA clone of the MART-1/Melan-A gene from DM6 melanoma cells. The entire open-reading frame for each of these cDNA's was sub-cloned into a modified pSC11 vector (Ref Hahn JEM 1991) adjacent to the vaccinia P7.5 early/late promoter using standard recombinant DNA methods. Standard dideoxy sequencing was used to confirm insertion and orientation. A recombinant vaccinia virus expressing the protein encoded by this gene (vac-Pmel-17) was generated using published methods (Ref Macket J. Virol 1984). Briefly, CV-1 cells were infected with the parental WR strain of vaccinia virus and transfected (Lipofectin, Gibco-BRL) with the pSC11.3-Pmel-17 plasmid. Thymidine-kinase negative recombinants were amplified in 143B TK- cells in the presence of bromodeoxyuridine (Sigma). Recombinants with beta-galactosidase activity were isolated and cloned through several rounds of plaque purification. Large-scale stocks were produced, sucrose purified, and titered in CV-1 cells.

The resulting recombinant vaccinia viruses were used to infect the lymphoblastoid cell lines C1R-A1, C1R-A2, C1R-A3, C1R-B7, and C1R-B8, where C1R is a human lymphoblastoid line devoid of native expression of HLA-A or HLA-B region molecules, but expressing low levels of HLA-C and MHC Class II molecules. In some cases EBV-transformed B cells with defined MHC expression were used for the infections. This resulted in transient expression of the antigens of interest.

These cells were assayed for recognition by CTL in CR51-release assays. As a negative control, target cells were also infected with a recombinant vaccinia virus with an irrelevant DNA insert (influenza nucleoprotein, NP). Thus, the cell lines listed above permit isolated evaluation of the expression of antigenic peptides in association with the common Class I MHC molecules HLA-A1, A2, A3, B7, and B8.

Evaluating recognition of target cells by CTL.

Reactivity was assessed by cytotoxicity in a 4-hour chromium release assay. Transient expression of individual melanoma differentiation antigens in non-melanoma cells was accomplished by infecting target cells with recombinant vaccinia viruses using 50 plaque forming units (titered on CV-1) per cell for 5–7 hours at 37° C. prior to $^{51}$Cr-labeling. Peptide-pulsed targets were generated by diluting peptides in RPMI and pre-incubating with $^{51}$Cr -labeled target cells for 2 hours prior to the addition of CTL. Assay wells containing peptide and target cells but no CTL were used as controls to rule out toxicity of the peptides themselves. Positive controls were the autologous tumor and known cross-reactive tumor lines. A negative control was uninfected C1R-MHC line and a C1R-MHC line transfected with a vaccinia construct expressing influenza nucleoprotein, vac-NP only. Briefly, $^{51}$Cr-labeled target cells were plated at 1–2×10$^3$ cells/well in triplicate on 96-well V-bottom plates (Costar, Cambridge, Mass.) with indicated ratio of effector cells in a final volume of 200 microliters. Wells containing either culture medium or 1M HCl in place of the effector cells served as spontaneous and maximum $^{51}$Cr-release controls, respectively. Plates were centrifuged at 100×g for 3 min and incubated at 37° C. for 4 h, after which 150 microliters of supernatant from each well was counted on a gamma counter (ICN). The percent specific lysis was calculated using the equation: [(experimental release—spontaneous release)/(maximum release—spontaneous release)]×100. Vaccinia infected targets were generated by infecting cells with 50 pfu/cell of appropriate recombinant vaccinia virus at 37° C. for 5 h, prior to $^{51}$Cr-labeling.

Peptide synthesis and Reconstitution with synthetic peptides:

Peptide sequences were selected from the reported human sequence of tyrosinase, based on predicted HLA-A1 binding motifs (see table 10). These peptides were synthesized by standard Fmoc chemistry using a Gilson model AMS422 peptide synthesizer. Biologically active peptides identified at initial screening were purified to >98% by reversed-phase HPLC on a Vydac C-4 column with 0.05% trifluoroacetic acid (TFA): water and an acetonitrile gradient and then re-evaluated in cytolysis assays. Peptides were reconstituted in CTL assay medium (RPMI 1640, 10% FCS, antibiotics) and pre-incubated for 2 h with 2×10$^3$ $^{51}$Cr labeled target cells in 100 microliters/well in 96-well plates. Effector cells were added in 100 microliters assay medium for a final effector to target (E:T) ratio of 20:1 and the remainder of the assay was performed as in standard chromium release assays described above. Wells containing peptide and target cells but no CTL were used as controls to rule out toxicity of the peptides themselves. Initial experiments were performed with unpurified synthetic peptides. Biologically active peptides identified at initial screening were then purified to >98% by reversed-phase HPLC on a Vydac C-4 column with 0.05% trifluoroacetic acid:water and an acetonitrile gradient, then re-evaluated in CTL assays.

Results

Melanoma-reactive CTL lines recognize MHC-associated peptides from several melanocytic differentiation antigens The CTL lines listed in Table 111 were evaluated for recognition of peptides derived from the 3 melanocytic tissue differentiation antigens listed above, in chromium-release assays, by transient infection with vaccinia constructs encoding those genes. Examples of their reactivity against HLA-matched allogeneic melanomas are shown in FIG. 1. A summary of these results with vaccinia constructs are listed in Table 112 and are shown in FIG. 2. Responses to tyrosinase peptides were observed in half of cases. In addition, responses to MART-1 and gp100 peptides were observed in a smaller set of CTL lines.

At least two of the HLA-A1+ CTL lines recognized tyrosinase peptides in an HLA-A1-restricted manner.

VMM12 CTL and VMM15 CTL were assayed initially on autologous EBV-B cells as targets. Reactivity against tyrosinase was observed, so additional studies were performed to confirm the reactivity and to determine the MHC restriction (FIG. 2). C1R cells that express selected Class I MHC molecules only were used as target cells. As seen in FIG. 2, C1R-A1 cells infected with vac-tyrosinase are recognized by VMM12 and VMM15 CTL, confirming that one or more tyrosinase-derived peptides are recognized by VMM12 and VMM15 CTL in association with HLA-A1.

The peptide representing residues 243–251 of tyrosinase reconstitutes an epitope for VMM15 CTL.

Figure 3:
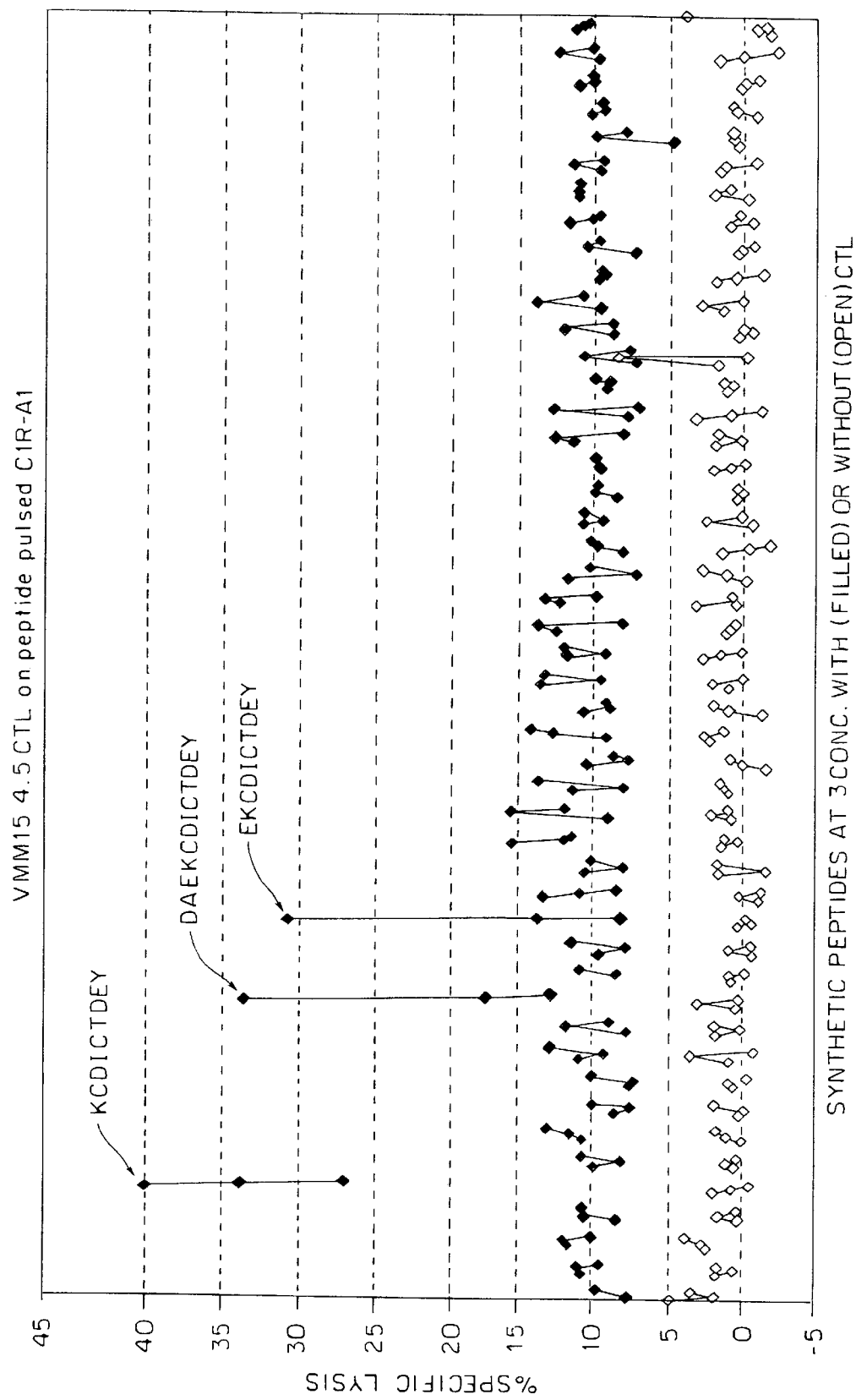

A set of peptides were synthesized from the defined amino acid sequence of tyrosinase, including 9-mers and longer peptides, with tyrosine (Y) at the C-terminal position and T, S, or M at position 2 and/or D, E, A, or S at position 3. These were assayed for their ability to reconstitute epitopes for melanoma-reactive CTL VMM12 and VMM15. C1R-A1 cells were pulsed with the peptide at concentrations ranging from 0.1 to 10 uM in normal assay medium (RPMI+10% FCS), then evaluated for recognition in a chromium-release assay. As shown in FIG. 3, three peptides were recognized by VMM15 CTL, all containing the sequence KCDICTDEY (SEQ ID NO:19) (tyrosinase residues 243–251). The most effective, even at the lowest concentration tested, was the 9-mer peptide KCDICTDEY (SEQ ID NO:19), but also recognized were a ten-mer, EKCDICTDEY (SEQ ID NO:37), and a 13-mer, DAEKCDICTDEY (SEQ ID NO:10) (FIG. 3).

Figure 4:
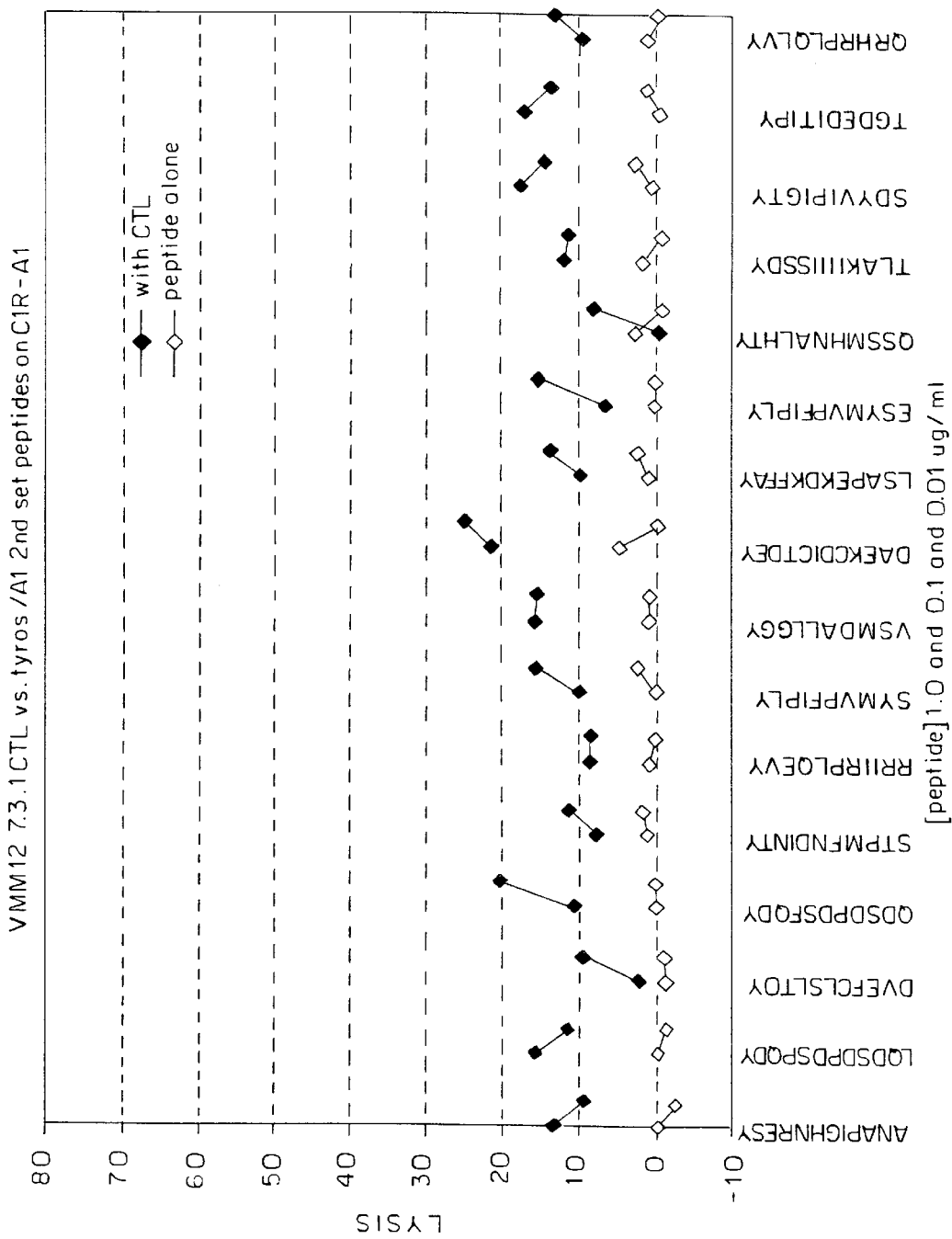
Figure 6:
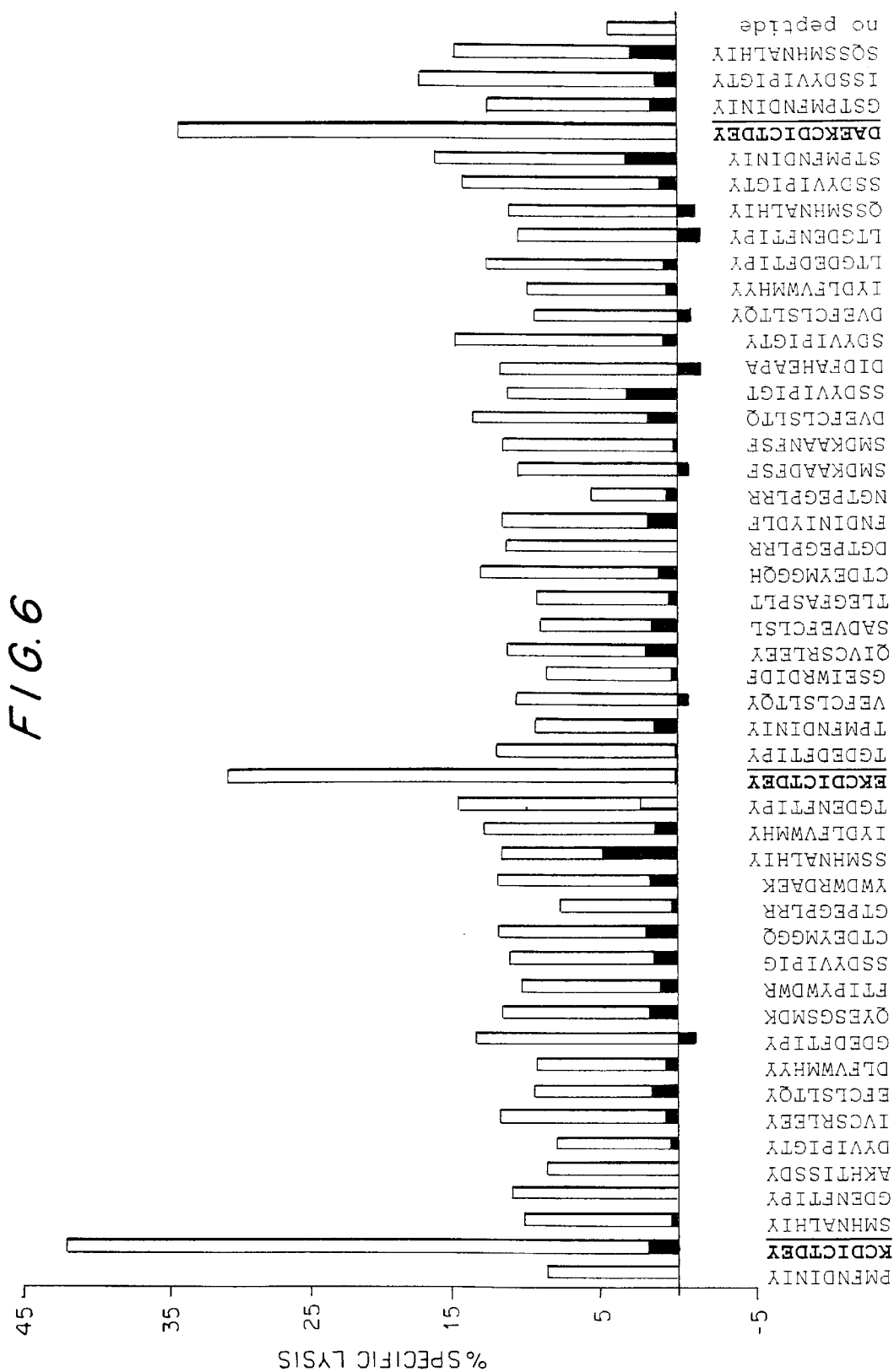

Similar reactivity was seen with VMM12 CTL as well, suggesting that KCDICTDEY (SEQ ID NO:19) is a shared antigen on human melanoma cells expressing HLA-A1, against which multiple patients' CTL may be expected to react (FIG. 4). The location of this peptide in the intact protein tyrosinase is shown in FIG. 5.

Discussion

The peptide KCDICTDEY (SEQ ID No:19) appears to be recognized by CTL from at least two different patients, in association with HLA-A1. Although longer peptides also are reactive, the dominant response seems to be to KCDICTDEY (SEQ ID NO:19). This peptide is unusual in its large number of polar amino acid residues, including two aspartic acid residues, one glutamic acid residue, and two cystine residues. The tyrosine residue at position 9 and the aspartic acid at position 3 are important for binding to the MHC. By a computerized system for predicting the binding affinity of individual peptides to HLA-A1 (and other HLA haplotypes), see http://bimas.dcrt.nih.gov:80/cgi-bin/molbio/ken_ parker_comboform (The algorithm for this software is discussed in Parker, et al., J. Immunol., 152:163 (1994)), this peptide is predicted to the be the tyrosinase peptide with highest affinity for HLA-A1, which may make it useful for immunization after pulsing on antigen-presenting cells.

KCDICTDEY (SEQ ID NO:19) is associated with half-maximal lysis at approximately 1 ug/ml (1 uM). The potency of this activity may be increased by various amino acid substitutions as taught above.

There have been two peptides described as epitopes for melanoma-reactive HLA-A1-restricted CTL. They are the MAGE-1 and MAGE-3 peptides EADPTGHSY (SEQ ID NO:88) and EVDPIGHLY (SEQ ID NO:90). While these have substantial potential value as immunogens, only a subset of melanoma patients express them. Most other MHC-associated peptide epitopes are HLA-A2 associated. However, HLA-A1 is expressed in approximately 29% of patients in this country. We have previously described an HLA-A3-associated epitope from gp100, ALLAVGATK (SEQ ID NO:80). Now, with defined peptide epitopes known, it is possible to consider the use of a multivalent peptide vaccine, where all patients expressing either HLA-A1, HLA-A2, or HLA-A3, which is approximately 70% of the patients at risk, may be treated with specific vaccine therapy.

TABLE 111

CTL lines studied for recognition of target cells infected with vaccinia constructs encoding Pme117/gp100, Tyrosinase, or MART-1/MelanA

| Melanoma Patient ID | Class I MHC expression | Target cell | MHC shared with target | Pme-117-reactive | Tyro-sinase-reactive |
|---|---|---|---|---|---|
| VMM12 | A1, A3, B7, B14 | VMM12-EBV | A1, A3, B7, B14 | 0 | Yes |

TABLE 111-continued

CTL lines studied for recognition of target cells
infected with vaccinia constructs encoding Pme117/gp100,
Tyrosinase, or MART-1/MelanA

| Melanoma Patient ID | Class I MHC expression | Target cell | MHC shared with target | Pme-117-reactive | Tyro-sinase-reactive |
|---|---|---|---|---|---|
| | | VMM15-EBV | A1 | 0 | Yes |
| | | C1R-A1 | A1 | — | Yes |
| | | C1R-A3 | A3 | — | 0 |
| | | C1R-B7 | B7 | — | 0 |
| VMM15 | A1, A25, B8, B18 | VMM15-EBV | A1, A25, B8, B18 | 0 | Yes |
| | | C1R-A1 | A1 | — | Yes |
| | | C1R-B8 | B8 | — | +/− |
| | | VMM38-EBV | B18 | — | 0 |
| VMM10 | A3, A25, B62, C1, C4 | VMM15-EBV | A25 | 0 | +/− |
| | | VMM12-EBV | A3 | 0 | 0 |
| | | VMM16-EBV | C1, C4 | 0 | 0 |
| VMM30 | A1, A2, B27, B57, C2, C6 | VMM30-EBV | A1, A2, B27, B57, C3 | 0 | Yes |
| VMM14 | A1, A25, B8, B48 | VNM15-EBV | A1, A25, B8 | 0 | Yes |
| VMM21 | A1, A2, B7, B37 | VMM21-EBV | A1, A2, B7, B37 | 0 | 0 |
| VMM18 | A3, A31/33, B60, C3 | VMM18-EBV | A3, A31/33, B60, C3 | Yes | 0 |
| | | VMM12-EBV | A3 | Yes | 0 |
| | | C1R-A3 | A3 | Yes | — |
| | | VMM17-EBV | A33? | 0 | — |
| VMM19 | A24, B35, B55 | VMM19-EBV | A24, B35, B55 | +/− | 0 |
| DM331 | A1, A2, B15, B62 | VMM12-EBV | A1, A2, B15, B62 | 0 | 0 |
| VMM39 | A2, A3, B7, B44 | VMM12-EBV | A3, B7 | 0 | 0 |
| | | VMM30-EBV | A2 | 0 | 0 |

— = not tested
+/− = results are equivocal and need further investigation.

TABLE 112

Summary of CTL reactivities observed

| Patient ID | Source of CTL epitope | Restricting Class I MHC molecule |
|---|---|---|
| VMM10 | — | n/a |
| VMM12 | Tyrosinase | A1 |
| VMM14 | Tyrosinase | unknown |
| VMM15 | Tyrosinase | A1 |
| | MART-1 | unknown |
| VMM18 | Pme117 | A3 |
| | MART-1 | A3 |
| VMM19 | — | n/a |
| VMM21 | MART-1 | unknown |
| VMM30 | Tyrosinase | unknown |
| VMM39 | — | n/a |
| DM 331 | — | n/a |

EXAMPLE A1–2

CTL from HLA-A1+ human melanoma patients recognize tyrosinase-derived epitopes

Melanoma-reactive CTL lines were generated from human melanoma patients and tested for reactivity against autologous and allogeneic melanomas and autologous and allogeneic B-LCL following transient expression of the melanocyte differentiation proteins Pmel-17/gp100, MART-1/Melan-A, and tyrosinase. These CTL lines were tested as soon as residual NK and lymphokine activated killer activities were low and reactivity against autologous melanoma could be demonstrated, typically at 25 to 40 days in culture. As shown in Table 201, reactivity against tyrosinase-derived epitopes was observed for five of the six HLA-A1+ CTL lines. The one HLA-A1$^+$ CTL line that did not demonstrate reactivity against tyrosinase was derived from a patient whose tumor line, DM331, does not express tyrosinase or any other defined melanocyte differentiation proteins. Thus, tyrosinase-derived epitopes were recognized by CTL from all HLA-A1-positive patients whose tumors express tyrosinase. CTL lines from melanoma patients recognize tyrosinase encoded peptides restricted by HLA-A1

Of the HLA-A1$^+$ CTL lines recognizing tyrosinase epitopes, VMM12 CTL and VMM15 CTL lines were sufficiently available to permit detailed analysis. To determine which of the class I MHC alleles was responsible for presentation of tyrosinase epitopes to these two CTL lines, the tyrosinase-vaccinia constructs were evaluated in C1R cells transfected with one of the class I MHC alleles expressed on the patient's tumor. Following infection with the recombinant vaccinia virus expressing full-length tyrosinase, the HLA-A1 transfectant of C1R was recognized and lysed by VMM12 CTL and VMM15 CTL, but HLA-A3, -B7, and -B8C1R transfectants were not recognized under identical conditions. Thus, HLA-A1 is a restriction element for the recognition of tyrosinase by CTL lines VMM12 and VMM15.

VMM15 CTL were also evaluated for recognition of a panel of target cells. Lysis depended on the expression of HLA-A1 and the expression of tyrosinase. In particular, there is no lysis of the tyrosinase-negative melanoma Na8Mel, but there was significant lysis of the tyrosinase-transfected cell line Na8Mel+Tyr. Both Na8Mel and Na8Mel+Tyr express HLA-A1. The melanoma line DM331, which is HLA-A1+ and tyrosinase negative, is not lysed, whereas the HLA-A1+/tyrosinase+melanomas HT144 and VMM14 are lysed. VMM12 tumor cells variably lose expression of HLA-A1, and are not lysed in this assay but have been lysed by VMM15 CTL in other assays when HLA-A1 is expressed. DM6 is a tyrosinase+/HLA-A1-negative melanoma and is not lysed. In several other assays, SkMel24, another tyrosinase-negative, HLA-A1+ melanoma, was not lysed by this CTL line. Thus, tyrosinase expression was both necessary and sufficient for lysis of HLA-A1+ target cells by VMM15 CTL.

HLA-A1-restricted CTL recognize peptides containing the sequence KCDICTDEY (SEQ ID NO:19)

To identify the HLA-A1-restricted peptide epitopes recognized by VMM12 and VMM15 CTL, we scanned the tyrosinase protein sequence for peptides matching published HLA-A1 binding motifs. For nine-residue peptides, these motifs can be summarized as follows: threonine, serine, or methionine at position two; aspartate, glutamate, alanine, or serine at position three; and tyrosine at the carboxyl terminus. Also included in this evaluation were peptides containing more than 9 residues. Since the C-terminal tyrosine residue appears to be invariant for HLA-A1 binding peptides, we predicted that longer peptides may retain the C-terminal tyrosine but would be extended from the N-terminus. In a previous study of HLA-A2 restricted epitopes, a post-translational modification of tyrosinase involving a deamination reaction resulted in the conversion of an asparagine residue into aspartate. Therefore, in addition to testing the wild-type version of potential HLA-A1 binding peptides that contained N-linked glycosylation sites (..N-x-S/T..), we also tested variants of these peptides with aspartate (D) substituted for asparagine (N). With these considerations, over 100 peptides matching this motif and ranging in length from eight to twelve amino acids were synthesized and tested for their ability to reconstitute the epitope recognized by VMM15 CTL. None of the first set of peptides tested had activity; so additional peptides synthesized included a number that fit the binding motif loosely: containing only threonine or serine at position 2, only an acidic residue at position 3, or only the C-terminal tyrosine. In one experiment, three of 48 peptides tested were recognized: KCDICTDEY (SEQ ID NO:19), DAEKCDICTDEY (SEQ ID NO:10), and EKCDICTDEY (SEQ ID NO:37), all of which contained the core nonamer sequence KCDICTDEY (SEQ ID NO:19) (FIG. 5). These three peptides containing the KCDICTDEY (SEQ ID NO:19) sequence will, collectively, be referred to as KCDICTDEY-related (SEQ ID NO:19) peptides.

These three synthetic peptides were purified by HPLC, and evaluated in a dose-titration assay (FIG. 8). Recognition of C1R-A1 cells pulsed with each of these peptides was indistinguishable by VMM15 CTL and, at higher peptide concentrations, targets pulsed with each of these three peptides were recognized at levels comparable to the autologous tumor cells (FIG. 8). Similarly, we found that lysis of target cells pulsed with DAEKCDICTDEY (SEQ ID NO:10) (50 $\mu$g/ml) can be inhibited by competition with the wild-type VMM15 tumor cells in a cold target inhibition assay. Thus, the epitope reconstituted by a KCDICTDEY-related (SEQ ID NO:19) peptide corresponds to the epitope presented naturally on VMM15 tumor cells. However, the concentration of peptide required for reconstitution was high, with half-maximal lysis observed at 2 $\mu$g/ml (approximately 2 $\mu$M). These peptides are distinguished from most other CTL epitopes by containing two cysteine residues. Since most other defined epitopes for melanoma-reactive CTL can be reconstituted at nanomolar concentrations or lower this raised a question of whether the KCDICTDEY-containing (SEQ ID NO:19) peptides actually constituted the true epitope for these CTL, and whether they were naturally processed and presented in association with HLA-A1.

Identification of DAEKCDICTDEY (SEQ ID NO:10) as the naturally presented epitope in association with HLA-A1 on melanoma cells. To determine whether any of the KCDICTDEY-containing (SEQ ID NO:19) peptides are actually processed and presented by melanoma cells in association with HLA-A1 molecules, HLA-A1-associated peptides were isolated, reduced in DTT to remove possible modifications on the sulfhydryl groups of cysteine residues, then fractionated by HPLC. Synthetic forms of the three KCDICTDEY-containing (SEQ ID NO:19) peptides were also fractionated under identical conditions to identify their elution point relative to the naturally-processed peptides in the tumor cell extracts. Fractions 17–20 were identified as representing the elution points for all of these KCDICTDEY-containing (SEQ ID NO:19) peptides. The nonamer and decamer were found in fractions 17 and 18; the undecamer was found in fraction 18, the dodecamer was found in fractions 19 and 20. Thus, aliquots of those fractions were evaluated by tandem mass spectrometry to determine whether any of the KCDICTDEY (SEQ ID NO:19) peptides were present in the extracts. CAD spectra were generated for species with m/z ratios 545, 610, 645, and 702, corresponding to the nonamer (KCDICTDEY (SEQ ID NO:19)), decamer (EKCDICTDEY (SEQ ID NO:37)), undecamer (AEKCDICTDEY residues 2–12 of SEQ ID NO:10), and dodecamer peptides (DAEKCDICTDEY (SEQ ID NO:10)), respectively, in each of these fractions. An ion with m/z 702 was identified in fraction 20, and the CAD spectrum of that species confirmed its identity as DAEKCDICTDEY (SEQ ID NO:10), the dodecamer peptide recognized by VMM15 CTL. In addition, the decamer peptide EKCDICTDEY (SEQ ID NO:37) was also identified, but at a lower copy number, in this extract. Neither the nonamer peptide KCDICTDEY (SEQ ID NO:19) nor the undecamer peptide AEKCDICTDEY (residues 2–12 of SEQ ID NO:10) was found.

These KCDICTDEY-containing (SEQ ID NO:19) peptides include a high number of acidic residues (two aspartic acids (D) and one glutamic acid (E)) and two cysteine (C) residues. When the DAEKCDICTEY (SEQ ID NO:10) peptide was identified by mass spectrometry, it contained a disulfide bond between the two cysteine residues, which could be reduced by treatment with dithiothreitol (DTT) such that the linear configuration with two free cysteine residues was returned. The internal disulfide bond forms a cyclized central portion of the molecule and results in a loss of two hydrogen atoms, and, therefore, ions containing both cysteines are two mass units smaller than in the reduced form. In addition, in the cyclized peptide, both cysteine residues remain together after collision activated dissociation; thus, the CAD spectrum for this species lacks the $b_5$(DAEKC+), $b_6$(DAEKCD+), and $b_7$(DAEKCDI+) ions as well as the $y_5$(+CTDEY), $y_6$(+ICTDEY), and $y_7$(+DICTDEY) ions. On the other hand, the CAD spectrum for the reduced species contains detectable $b_5$, $b_6$, $b_7$, and $y_5$, ions. The CAD spectrum for the reduced species is identical to the CAD spectrum for the synthetic DAEKCDICTDEY (SEQ ID NO:10) peptide.

Substitution of serine or alanine for the more N-terminal cysteine residue markedly enhances reconstitution of the CTL epitope By direct evaluation of peptides eluted from HLA-A1 molecules, it was not possible to determine definitively which of the KCDICTDEY-related (SEQ ID NO:19) peptides was naturally processed and presented in association with HLA-A1, suggesting that they are present in low quantity or have been modified. Subsequent studies thus addressed potential modifications of both the nonamer KCDICTDEY (SEQ ID NO:19) and the dodecamer DAEKCDICTDEY (SEQ ID NO:10). Spontaneous modification of free cysteine residues by disulfide bond formation will occur in medium containing cystine (C-C) or glutathione, such as RPMI or human serum. Thus, we examined the effect of substituting serine or alanine for one or both cysteine residues in the synthetic KCDICTDEY-related (SEQ ID NO:19) peptides in an effort to prevent the formation of disulfide bonds.

The synthetic nonamer with the wild-type sequence (KCDICTDEY (SEQ ID NO:19)) induced half-maximal lysis at 2 to 20 $\mu$M. However, when the cysteine closer to the N-terminus (position 2) was replaced with serine or alanine (KSDICTDEY (SEQ ID NO:73) or KADICTDEY (SEQ ID NO:70)), half-maximal lysis was observed after incubation of targets with 100- to 1000-fold lower concentrations (2 and 20 nM, respectively; FIG. 8A). On the other hand, peptides with alanine or serine substituted for the cysteine distal to the N-terminus, at position (KCDISTDEY (SEQ ID NO:74) or KCDIATDEY (SEQ ID NO:71)) were not discernibly more effective than the wild-type peptide. Nonamer peptides with alanine or serine substituted for both cysteine residues were actually less effective than the wild-type peptide.

Similarly, the dodecamer with the wild-type sequence (DAEKCDICTDEY (SEQ ID NO:10)) required 10 $\mu$M for half-maximal sensitization of target cells for lysis. However, when the cysteine closer to the N terminus (position 5) was replaced with alanine (DAEKADICTDEY (SEQ ID NO:76)), half-maximal lysis was observed after incubation of targets with approximately 100 nM (FIG. 5B). On the other hand, alanine substitution for the cysteine closer to the C-terminus, at position 8 (DAEKCDIATDEY (SEQ ID NO:77)), prevented recognition at every concentration tested. These data demonstrate that the more C-terminal cysteine (residue 247 of tyrosinase) is critical to the formation of the CTL epitope, raising the possibility that spontaneous modifications of that residue by disulfide bond formation may be integral to the actual epitope.

Because of the similar effects on CTL recognition observed with amino acid substitutions for the more N-terminal cysteine residue in both the dodecamer DAEKCDICTDEY (SEQ ID NO:10) and the nonamer KCDICTDEY (SEQ ID NO:19), and because of the similar dose-titration curves observed for CTL recognition (FIG. 8), we hypothesized that residues 243 to 251 (KCDICTDEY (SEQ ID NO:19)) of both peptides adopt a similar conformation when bound to HLA-A1. A cold target inhibition assay was performed with peptide-pulsed target cells to test that hypothesis. As shown in FIG. 9, unlabeled target cells pulsed with the dodecamer effectively inhibited lysis of Cr-labeled targets pulsed with the nonamer, at a level equivalent to the inhibition induced by cold targets pulsed with the nonamer itself. Recognition of labeled targets pulsed with the dodecamer DAEKSDICTDEY (SEQ ID NO:79) was similarly inhibited by unlabeled targets pulsed with the nonamer KSDICTDEY (SEQ ID NO:73). These data suggest that the conformation of the peptide-MHC complex within the region recognized by the TCR of VMM15 is, therefore, similar or identical for the nonamer and dodecamer peptides.

Discussion

We have shown previously that the melanocyte differentiation protein Pmel-17/gp100 is a source of epitopes for melanoma-reactive CTL restricted by HLA-A*0201 and HLA-A3. Using vaccinia constructs encoding this protein and CTL lines from patients with varied MHC profiles, we identified the Pmel-17/gp100 peptide ALLAVGATK (SEQ ID NO:80) as an epitope for A3-restricted CTL. We now provide evidence that tyrosinase-derived peptides are frequently recognized by HLA-A1+ CTL. Among HLA-A1+ patients, CTL recognition of tyrosinase epitopes was evident in all cases, except when the autologous tumor itself failed to express tyrosinase. By screening over 100 synthetic peptides derived from the tyrosinase sequence, we found that the peptides KCDICTDEY (SEQ ID NO:19), EKCDICTDEY (SEQ ID NO:37), and DAEKCDICTDEY (SEQ ID NO:10) were all recognized by A1-restricted melanoma-reactive CTL.

The naturally processed epitope may be a nonamer or may be as long as a dodecamer. Peptides containing 12 residues are uncommon among described class I MHC-associated peptides, and we are unaware of previously reported examples of dodecamer peptides representing CTL epitopes. Dodecamer peptides have been identified in association with cells containing Ag-processing defects, where a TAP-independent pathway has been implicated in their processing and presentation. Also, in cells with normal Ag-processing machinery, dodecamers associated with HLA-A1 and HLA-A11 have been described. A dodecamer from cytochrome C oxidase that is associated with HLA-A1 contains putative anchor residues at positions 3 and 12 (YTDYGGLIFNSY (SEQ ID NO:104)), see Engelhard, et al., Currl. Opin. Immunol., 6:13 (1994). Thus, that peptide is predicted to bind to the HLA-A1 molecule with a kink between residues 3 and 12 to allow for the extra length. The synthetic DAEKCDICTDEY (SEQ ID NO:10) peptide, however, could potentially bind to HLA-A1 in either of two conformations. While the tyrosine residue at the C terminus is almost certain to function as the C-terminal anchor residue, the motif requirement for an acid residue at position 3 could be satisfied either by the glutamic acid (E) at position 3 or by the aspartic acid (D) at position 6. In the former case, the central portion of the peptide would have to be kinked and would extend out of the plane of the binding groove, a conformation that could b stabilized or induced by a disulfide bond between the two cysteine residues. If, however, the aspartic acid residue at position 6 functions as an anchor residue, the three N-terminal residues (DAE) would be expected to extend up and out of the binding groove, while the rest of the peptide interacts in the groove in a conformation resembling that of the nonamer peptide.

If the dominant conformation of the dodecamer is kinked, then it would be anticipated that CTL recognition would be sensitive to the peptide structure between residues 5 and 12, and that CTL recognizing that peptide would not cross-react with target cells pulsed with the synthetic nonamer lacking the N-terminal DAE residues. However, CTL reactive against the dodecamer were equally reactive against both the decamer EKCDICTDEY (SEQ ID NO:37) and the nonamer KCDICTDEY (SEQ ID NO:19). While these studies were performed with a CTL line, which probably contained distinct CTL subpopulations, our cold target inhibition assays provide evidence that both the nonamer and dodecamer peptides are recognized by the same CTL. We have also observed that dodecamers containing glycine substituted for alanine or glutamate at positions 2 and 3 were recognized at levels comparable to those of the wild-type peptide (data not shown). Therefore, the nonamer and dodecamer peptides probably exist in similar conformation when bound to HLA-A1, such that the three amino-terminal residues of the dodecamer would extend out of the binding groove, and residues 4 through 12 would be expected to lie flat, in a manner analogous to the configuration expected for the nonamer peptide.

Regardless of the precise length and conformation of the peptides bound to the MHC, the KCDICTDEY-related (SEQ ID NO:19) peptides are unusual in containing two cysteine residues. In general, sulfhydryl groups on cysteine residues are susceptible to derivatization with sulfhydryl groups on other biologic molecules such as cystine or glutathione, both of which are present in human serum and RPMI. Especially, since formation of disulfide bonds is favored at mildly basic pH and in the presence of oxygen, both the in vivo setting (pH 7.4, $pO_2$ 40–100 mm Hg) and the standard culture conditions in vitro would favor modification of cysteine residues with exposed side chains. To assess the roles of the two cysteine residues in the KCDICTDEY-related (SEQ ID NO:19) peptides with respect to T cell recognition, a series of experiments was performed comparing the naturally occurring peptides with peptides containing amino acid substitutions. Substitution of serine or alanine for the more N-terminal cysteine prevents potential modifications of that residue, including formation of an internal disulfide bond. After making such a substitution, both the dodecamer and the nonamer were capable of reconstituting CTL epitopes at concentrations 2 to 3 logs lower than the unsubstituted peptides. Thus, we hypothesize that disulfide bonds involving this more N-terminal cysteine residue negatively affect binding of exogenous peptide to the HLA-A1 molecule, and that in the naturally processed peptide, the cysteine residue at that position (position 2 of KCDICTDEY (SEQ ID NO:19), residue 244 of tyrosinase) is not modified, perhaps being protected within the binding groove of HLA-A1. Similarly, the more C-terminal cysteine would be anticipated to point upward and to have an exposed side chain. In cystine- and glutathione-rich medium, such as RPMI (in vitro) or human serum (in vivo), the more C-terminal cysteine may well be modified by cysteinylation or by derivatization with another molecule containing a sulfhydryl group. T cell recognition of that epitope may depend on such a modification. Indeed, as shown in FIG. 8, recognition by VMM15 CTL is acutely sensitive to the presence of a cysteine residue at this position (KSDICTDEY (SEQ ID NO:73) vs KSDISTDEY (SEQ ID NO:75)).

Peptides load onto NHC molecules in the oxidative environment of the endoplasmic reticulum (ER), where modification of cysteine residues by reversible formation of disulfide bonds would be expected. However, at least one enzyme in the ER, protein disulfide isomerase, can catalyze dissociation of disulfide bonds.

The KCDICTDEY (SEQ ID NO:19) consensus sequence is unusual in the large number of polar amino acid residues, including two aspartic acid residues, one glutamic acid residue, and two cysteine residues. The tyrosine residue at the C-terminus (position 9 of KCDICTDEY (SEQ ID NO:19)), and the aspartic acid at position 3 of the KCDICTDEY (SEQ ID NO:19) peptide are critical residues for binding to the MHC; so we conclude that the A1 molecule binds KCDICTDEY (SEQ ID NO:19) in its binding groove and that when the dodecamer peptide DAEKCDICTDEY (SEQ ID NO:10) binds to HLA-A1, the N-terminal residues DAE extend out of the pocket. Alternatively, one could postulate that this peptide could bind to HLA-A1 in the cyclized conformation caused by disulfide linkage of the 2 cysteine residues. The glutamic acid (E) residue at position 3 and the tyrosine at position 12 could fit the binding motif if enough of a kink were created in the peptide by the disulfide bond. However, CTL reactive against this epitope were equally reactive against the nonamer KCDICTDEY (SEQ ID NO:19) (FIG. 7), suggesting that the configuration of the epitope is the same for these two peptides, and that the epitope is independent of the excess residues extending out of the A1-binding groove. This is further supported by the finding that substitution of serine or alanine for the cysteine at residue 244, which would prevent the internal disulfide bond, dramatically increased the ability of this peptide to reconstitute the CTL epitope. Thus, the CTL appear to have been sensitized against an epitope in which the peptide has not formed a disulfide bond. Further, since the nonamer and the dodecamer are equally well recognized by CTL, the epitope appears to be independent of the N-terminal 3 amino acids (DAE).

Once peptides are dissociated from the MHC, especially in the presence of oxygen or in slightly basic conditions (eg., exposed to air, or in vivo conditions: pH 7.4), modifications of cysteine residues by formation of disulfide bonds may be anticipated. At a molecular level, proximity likely favors formation of the internal disulfide bonds, resulting in cyclization of these KCDICTDEY (SEQ ID NO:19) peptides. It is also possible that either of the cysteine residues in this peptide may be modified in the endoplasmic reticulum, such as by addition of an acyl group, or that modification of exposed sulfhydryl groups may occur while the peptide:MHC complex is exposed to serum components in vivo, where cyclization would be inhibited by association with the MHC. The more C-terminal cysteine would be easily accessible to derivatization by glutathione or cystine. Such modifications were not directly identified by mass spectrometry, but it remains a possibility that the optimal epitope in vivo includes a spontaneous modification of the more C-terminal cysteine residue.

We predict that those peptides not containing internal disulfide bonds or other modifications of the more N-terminal cysteine are those capable of binding to the nascent MHC molecules for presentation at the cell surface. Whether there are specific molecular chaperones favoring this process in the ER remains to be demonstrated.

Aside from what happens during normal Ag processing and presentation, synthetic peptides free in solution are susceptible to modifications of cysteine residues by formation of disulfide bonds, especially in the presence of oxygen or in slightly basic conditions (e.g., exposed to are or in vivo). Because of the proximity of the two cysteine residues, the likelihood of interaction between them probably exceeds the likelihood of interaction with another molecular species in solution. In fact, intramolecular disulfide bonds between cysteine residues in short peptides containing the sequence —CXYC— are highly favored at concentrations up to 200 $\mu$M in neutral pH solutions and are facilitated by air oxidation of the cysteine residues. The resulting cyclized form of KCDICTDEY-related (SEQ ID NO:19) peptides may not be capable of binding to the HLA-A1 molecule or, if bound, would probably result in a molecular conformation different from that of the epitope recognized by CTL. The fact that cyclization and other cysteine modifications occur readily may well explain the high concentration of KCDICTDEY-related (SEQ ID NO:19) peptides required for sensitization of C1R-A1 target cells in vitro and would imply similar results in vivo if a tumor vaccine using the wild-type peptide were administered.

On the other hand, peptides containing substitutions of serine or alanine for the more N-terminal cysteine induced half-maximal lysis of target cells at 1 to 20 nM, which compares favorably to peptide concentrations required for reconstitution of the MAGE-1 epitope EADPTGHSY (SEQ ID No:88) on HLA-A1 (half maximal lysis at ~10 nM) and the MART-1 peptide AAGIGILTV (SEQ ID NO:86) on HLA-A*0201 (half-maximal lysis at ~1–100nM). We believe that replacement of the more N-terminal cysteine probably enables purified peptides to bind to cell surface MHC molecules in a manner that more accurately mimics the configuration of peptides binding to nascent MHC molecules in the ER.

A concern with these KCDICTDEY-containing (SEQ ID NO:19) peptides, in terms of their potential usefulness in vaccine therapy, is that high concentrations were required for sensitization of target cells, with half-maximal lysis requiring approximately 2 uM concentrations. As described above, the two cysteine residues in these peptides likely explain some of their unusual features. The more C-terminal cysteine appears to be susceptible to interaction in vivo with sulfhydryl groups on biologic molecules such as cystine (present in human serum at 276 uM) or glutathione, and we have shown that the free peptide is capable of forming an intramolecular disulfide bond, resulting in cyclization of the peptide. Because of the proximity of these two cysteine residues, the likelihood of interaction between them probably exceeds the likelihood of interaction between one of them and another molecular species in solution. Intramolecular disulfide bonds between cysteine residues in short peptides containing the sequence —CxyC— are highly favored at concentrations at and below 200 uM in neutral pH solutions, and are facilitated by air oxidation of the cysteine residues. This cyclic form is not likely to be capable of binding to the HLA-A1 molecule, and its formation likely explains the high concentration required for sensitization of C1R-A1 target cells in vitro. Although the wild-type forms of these peptides require high concentrations for reconstitution, the substituted forms of these peptides induce half-maximal lysis of target cells at 1–20 nM concentrations, which compares favorably to reconstitution of the MAGE-1 epitope EADPTGHSY (SEQ ID NO:88) on HLA-A1, (half-maximal at approximately 10 nM) and the MART-1 peptide AAGIGILTV (SEQ ID NO:86) on HLA-A2 (at approximately 1–100 nM).

The significantly greater recognition of KADICTDEY (SEQ ID NO:70), KSDICTDEY (SEQ ID NO:73), and DAEKADICTDEY (SEQ ID NO:76) compared to KCDICTDEY (SEQ ID NO:19) and DAEKADICTDEY (SEQ ID NO:10) (FIGS. 8 and 9), supports the hypothesis that modifications of the more N-terminal cysteine residue interferes substantially with reconstitution of the epitope. In vivo, the naturally processed peptide would bind to the A1 molecule in the endoplasmic reticulum, and the more N-terminal cysteine would be protected from modification by being buried in the peptide-binding groove. Thus, substituting alanine or serine for cysteine in this position, when working with the free peptide, may protect that residue from modifications until the peptide can bind to the A1 molecule.

On the other hand, the more C-terminal cysteine is anticipated to point upwards towards the T cell receptor. This residue would be susceptible to modification at the cell surface while bound to the MHC molecule. In cystine-containing media, such as RPMI (in vitro) or human serum (in vivo), the more C-terminal cysteine may well be modified by cysteinylation or by derivitization with another molecule containing a sulfhydryl group. T-cell recognition of that epitope may depend partly on that modification, but may not require that modification.

In summary, three peptides containing the KCDICTDEY (SEQ ID NO:19) sequence are capable of reconstituting an epitope for HLA-A1-restricted melanoma-reactive CTL, but only the decamer EKCDICTDEY (SEQ ID NO:37) and the dodecamer DAEKCDICTDEY (SEQ ID NO:10) appear to be naturally processed and presented. Modifications of the more C-terminal cysteine residue by cysteinylation is likely to occur in vitro and in vivo, and this modification may well affect T-cell recognition. Modifications of the more N-terminal cysteine residue, however, are not believed to occur in vivo during normal processing and presentation but may occur when the peptide is free in solution. Modifications, such as intramolecular disulfide bonds leading to cyclization of the peptide, probably inhibit markedly the binding of that peptide to HLA-A1 at the cell surface. These observations have several implications. First, synthetic peptides that contain one or more cysteine residues may not be capable of reconstituting epitopes for CTL under standard conditions and may, therefore, be difficult to identify as CTL epitopes using standard methods unless the described modifications are anticipated. Second, preventing disulfide bond formation by modifying cysteine-containing peptides will improve their usefulness. For this particular peptide, it may be useful to immunize with the nonamer peptide containing serine or alanine at position 2, in place of the first cysteine.

As demonstrated by our data with the wild-type and substituted forms of KCDICTDEY-related (SEQ ID NO:19) peptides, cysteine residues can both positively and negatively affect MHC binding and/or T cell recognition. This suggests that potential problems with using cysteine-containing peptides as immunogens may be overcome by modifications of those cysteine residues. In particular, immunization with a peptide containing serine or alanine in place only of a non-essential cysteine may result in more effective loading onto MHC molecules of APC.

TABLE 201

| | | ANTIGEN REACTIVITY OBSERVED[α] | | | |
|---|---|---|---|---|---|
| CTL Line | MHC typing of CTL donor | MCH class I molecules evaluated | Pmel-17/ gp100 | MART-1/ Melan-A | tyrosinase |
| DM331 | –A1, 2; –B15, B62 | –A1, 2 | – | – | – |
| VMM12 | –A1, A3; –B7, B14 | * | – | – | + |
| VMM14 | –A1, 25; –B8, B48 | –A1, 25; –B8 | – | – | + |
| VMM15 | –A1, 25; –B8, B18 | * | + | + | – |
| VMM18 | –A3, 31/33; –B60; –C3 | * | + | + | – |
| VMM19 | –A24; –B35,55; –C3 | * | – | – | – |
| VMM21 | –A1, 2; –B7, 37 | * | – | + | + |
| VMM34 | –A3, 30; –B21, 70 | –A3 | – | – | – |
| VMM39 | –A2, 3; –B7 | –A2, 3; –B7 | – | – | – |
| VMM40 | –A1, 2; –B27, 57; –C37 | * | – | – | + |

Positive values indicate that target cells expressing the antigen listed, via a vaccinia construct, were lysed (at an E:T ratio of 30:1) at a level at least 10% higher than background lysis of the target cell infected with an irrelevant vaccinia construct.
*indicates all MHC were evaluated: these CTL were evaluated for recognition of autologous EBV-B cell lines infected with each of the vaccinia constructs listed.

Remarks

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

For immunological techniques generally, see Coligan, et al, *Current Protocols in Immunology* (NIH: 994); Harlow and Lane, *Antibodies:A laboratory Manual* (Cold Spring Harbor Lab.: 1988).

An immunogen is deemed not to occur in nature, even though its component epitopes do occur in nature, if the immunogen itself, as a single molecule, does not occur in nature. For example, a conjugate of KCDICTDEY (SEQ ID NO:19) to albumin does not occur in nature even though KCDICTDEY (SEQ ID NO:19) is a fragment of tyrosinase which is generated by the immune system processing of tyrosinase and complexes with MHC.

What is claimed is:

1. An immunogen which comprises a non-naturally occurring, cysteine-depleted CTL epitope which is a cysteine-depleted mutant of a naturally occurring CTL epitope, and which epitope elicits a greater CTL response than said naturally occurring epitope, differing from said naturally occurring epitope in that at least one cysteine residue of the naturally occurring epitope is replaced with a non-cysteine residue, and where said mutant epitope is otherwise either (a) identical to said naturally occurring epitope or (b) differs therefrom solely by (i) a single conservative substitution, and/or (ii) a single non-conservative substitution, wherein at least one of said cysteine-depleted epitopes is an A1-restricted epitope.

2. The immunogen of claim 1, which is an isolated, purified, or synthetic peptide of about 9 to about 15 residues in length.

3. The immunogen of claim 2 which is tumor-specific.

4. The immunogen of claim 2 wherein said naturally occurring epitope is SEQ ID NO:19, SEQ ID NO:37, or SEQ ID NO:10.

5. The immunogen of claim 2 wherein at least one cysteine of the naturally occurring epitope is replaced by Ala, Thr, Ser, Gly or Met.

6. A composition comprising a peptide according to claim 2 and a class I MHC molecule, whereby T lymphocytes may be stimulated by said peptide.

7. The immunogen of claim 2 in which the native epitope has two cysteines and both are replaced.

8. The immunogen of claim 2 in which the native epitope has two cysteines and only one is replaced.

9. The immunogen of claim 2 in which the native epitope has at least two cysteines.

10. The immunogen of claim 2 in which a Cys at position 2 of the native epitope is replaced.

11. The immunogen of claim 2 in which said mutant epitope is, save for such cysteine replacement, either identical to said naturally occurring epitope or different therefrom solely by a single conservative substitution.

12. the immunogen of claim 2 in which said mutant epitope is, save for such cysteine replacement, identical to said naturally occurring epitope.

* * * * *